United States Patent
Bernstein et al.

(10) Patent No.: US 11,439,667 B2
(45) Date of Patent: Sep. 13, 2022

(54) COMPOSITIONS AND METHODS FOR EXPANSION OF EMBRYONIC HEMATOPOIETIC STEM CELLS

(71) Applicant: Fred Hutchinson Cancer Research Center, Seattle, WA (US)

(72) Inventors: Irwin D. Bernstein, Seattle, WA (US); Brandon K. Hadland, Seattle, WA (US)

(73) Assignee: FRED HUTCHINSON CANCER CENTER, Seattle, WA (US)

( * ) Notice: Subject to any disclaimer, the term of this patent is extended or adjusted under 35 U.S.C. 154(b) by 268 days.

(21) Appl. No.: 16/656,342

(22) Filed: Oct. 17, 2019

(65) Prior Publication Data

US 2020/0046775 A1 Feb. 13, 2020

Related U.S. Application Data

(63) Continuation of application No. 15/939,199, filed on Mar. 28, 2018, now Pat. No. 10,463,698, which is a continuation of application No. 14/759,631, filed as application No. PCT/US2014/010463 on Jan. 7, 2014, now Pat. No. 9,956,249.

(60) Provisional application No. 61/750,332, filed on Jan. 8, 2013.

(51) Int. Cl.
| | |
|---|---|
| C07K 14/475 | (2006.01) |
| C07K 14/52 | (2006.01) |
| C07K 14/54 | (2006.01) |
| C12N 5/0735 | (2010.01) |
| C12N 5/0789 | (2010.01) |
| A61K 35/28 | (2015.01) |
| A61K 35/12 | (2015.01) |

(52) U.S. Cl.
CPC .............. *A61K 35/28* (2013.01); *C07K 14/52* (2013.01); *C12N 5/0606* (2013.01); *C12N 5/0647* (2013.01); *A61K 2035/124* (2013.01); *C07K 14/475* (2013.01); *C07K 14/54* (2013.01); *C07K 14/5403* (2013.01); *C07K 14/5412* (2013.01); *C07K 14/5431* (2013.01); *C12N 2501/10* (2013.01); *C12N 2501/125* (2013.01); *C12N 2501/145* (2013.01); *C12N 2501/15* (2013.01); *C12N 2501/2301* (2013.01); *C12N 2501/2303* (2013.01); *C12N 2501/2306* (2013.01); *C12N 2501/2311* (2013.01); *C12N 2501/26* (2013.01); *C12N 2501/42* (2013.01); *C12N 2533/52* (2013.01)

(58) Field of Classification Search
CPC .. C12N 5/0606; C12N 5/0696; C12N 5/0647; A61K 35/545; C07K 14/475; C07K 14/495; C07K 14/52; C07K 14/525; C07K 14/54; C07K 14/5412; C07K 14/5403; C07K 14/5431; C07K 16/24
See application file for complete search history.

(56) References Cited

U.S. PATENT DOCUMENTS

| | | | |
|---|---|---|---|
| 5,004,681 | A | 4/1991 | Boyse et al. |
| 5,648,464 | A | 7/1997 | Artavanis-Tsakonas et al. |
| 5,780,300 | A | 7/1998 | Artavanis-Tsakonas et al. |
| 5,849,869 | A | 12/1998 | Artavanis-Tsakonas et al. |
| 5,856,441 | A | 1/1999 | Artavanis-Tsakonas et al. |
| 6,627,191 | B1 * | 9/2003 | Bartelmez ............... A61P 43/00 424/93.7 |
| 7,399,633 | B2 | 7/2008 | Bernstein et al. |
| 2010/0183564 | A1 | 7/2010 | Boitano et al. |
| 2015/0353890 | A1 | 12/2015 | Bernstein et al. |
| 2018/0214491 | A1 | 8/2018 | Bernstein et al. |

FOREIGN PATENT DOCUMENTS

| | | |
|---|---|---|
| WO | WO2006047569 A2 | 5/2006 |
| WO | WO-2007039151 A1 * | 4/2007 |
| WO | WO2007095594 A2 | 8/2007 |
| WO | WO2011127470 A1 | 10/2011 |
| WO | WO2011127472 A1 | 10/2011 |
| WO | WO2014110020 A1 | 7/2014 |

OTHER PUBLICATIONS

Akhurst et al. Targeting TGF-beta signaling for therapeutic gain. Cold Spring Harbor Perspectives Biol 9: a022301, 2017 (30 total pages).*
Park et al. TGF-beta family signaling in embryonic stem cells. Int J Stem Cells 4(1): 18-23, 2011.*
Mukouyama, Y-S., et al., "In Vitro Expansion of Murine Multipotential Hematopoietic Progenitors From the Embryonic Aorta-Gonad-Mesonephros Region," Immunity 8(1):105-114, Jan. 1998.
Taipaleenmäki, H., et al., "The Crosstalk Between Transforming Growth Factor-β1 and Delta Like-1 Mediates Early Chondrogenesis During Embryonic Endochondral Ossification," Stem Cells 30(2):304-313 Feb. 2012.

(Continued)

*Primary Examiner* — Bridget E Bunner
(74) *Attorney, Agent, or Firm* — Christensen O'Connor Johnson Kindness PLLC

(57) ABSTRACT

The present invention relates to methods, kits and compositions for expansion of embryonic hematopoietic stem cells and providing hematopoietic function to human patients in need thereof. In one aspect, it relates to kits and compositions comprising a Notch agonist, one or more growth factors, and, optionally, an inhibitor of the TGFβ pathway. Also provided herein are methods for expanding embryonic hematopoietic stem cells using kits and compositions comprising a Notch agonist, one or more growth factors, and, optionally, an inhibitor of the TGFβ pathway. The embryonic hematopoietic stem cells expanded using the disclosed kits, compositions and methods include cells derived from an embryo (e.g., aorta-gonad-mesonephros region of the embryo), embryonic stem cells, induced pluripotent stem cells, or reprogrammed cells of other types. The present invention also relates to administering the embryonic hematopoietic stem cells expanded using a combination of a Notch agonist, one or more growth factors, and, optionally, an inhibitor of the TGFβ pathway to a patient for short-term and/or long-term in vivo repopulation benefits.

19 Claims, 10 Drawing Sheets

(56) References Cited

OTHER PUBLICATIONS

Office Action dated Mar. 10, 2021, issued in Canadian Application No. 2,897,499, filed Jan. 7, 2014, 6 pages.
Office Action dated Nov. 18, 2019, for Canadian Patent Application No. 2,897,499, 9 pages.
Karlsson, et. al., "Smad4 is Critical for Self-Renewal of Hematopoietic Stem Cells", The Journal of Experimental Medicine (JEM), The Rockefeller University Press, vol. 204, No. 3, Mar. 19, 2007, pp. 467-474.
Zhao, et al., "Expression, Purification, and Characterization of a Novel Soluble Form of Human Delta-like-1," App. Biochem. Biotech., vol. 160, No. 5, 2010, pp. 1415-1427.
Office Action dated Oct. 31, 2018, for Australian Patent Application No. 2014205662, 4 pages.
Office Action dated Apr. 5, 2019 for Australian Patent Application No. 2014205662, 2 pages.
Burns, "Hematopoietic stem cell fate is established by the Notch-Runx pathway," Genes & Development, vol. 19, No. 19, 2005, pp. 2331-2342.
Carlesso, et al., "Notch1-induced delay of human hematopoietic progenitor cell differentiation is associated with altered cell cycle kinetics," Blood, vol. 93, No. 3, 1999, pp. 838-848.
Dahlberg, et al., "Ex vivo expansion of human hematopoietic stem and progenitor cells," Blood, vol. 117, No. 23, 2011, pp. 6083-6090.
Dao, et al., "Adhesion to fibronectin maintains regenerative capacity during ex vivo culture and transduction of human hematopoietic stem and progenitor cells," Blood, vol. 92, No. 12, 1998, pp. 4612-4621.
de Lima, et al., "Mesenchymal Stem Cell (MSC) Based Cord Blood (CB) Expansion (Exp) Leads to Rapid Engraftment of Platelets and Neutrophils," Blood, vol. 116, 2010, Abstract 362, 4 pages.
Deftos, et al., "Correlating notch signaling with thymocyte maturation," Immunity, vol. 9, No. 6, 1998, pp. 777-786.
Delaney, et al., "Dose-dependent effects of the Notch ligand Delta1 on ex vivo differentiation and in vivo marrow repopulating ability of cord blood cells," Blood, vol. 106, No. 8, 2005, pp. 2693-2699.
Delaney, et al., "Notch-mediated expansion of human cord blood progenitor cells capable of rapid myeloid reconstitution," Nature Medicine, vol. 16, No. 2, 2010, pp. 232-237.
Ebihara, et al., "Generation of red blood cells from human embryonic/induced pluripotent stem cells for blood transfusion," Int. J. Hematol., vol. 95, No. 6, 2012, pp. 610-616.
Hadland, et al., "Endothelium and NOTCH specify and amplify aorta-gonad-mesonephros-derived hematopoietic stem cells," J. Clin. Invest., vol. 125, No. 5, 2015, pp. 2032-2045.
Jaroscak, et al., "Augmentation of umbilical cord blood (UCB) transplantation with ex vivo-expanded UCB cells: results of a phase 1 trial using the AastromReplicell System," Blood, vol. 101, No. 12, 2003, pp. 5061-5067.
Jehn, et al., "Cutting edge: protective effects of notch-1 on TCR-induced apoptosis," J. Immunol., vol. 162, No. 2, 1999, pp. 635-638.
Jones, et al., "Stromal expression of Jagged 1 promotes colony formation by fetal hematopoietic progenitor cells," Blood, vol. 92, No. 5, 1998, pp. 1505-1511.
Kimbrel and Lu, "Potential clinical applications for human pluripotent stem cell-derived blood components," Stem Cells Int., 2011, 11 pages.
Ko, et al., "Ex Vivo Expansion of Haematopoietic Stem Cells to Improve Engraftment in Stem Cell Transplantation," Methods in Molecular Biology, vol. 761, 2011, pp. 249-260.
Kumano, et al., "Notch1 but Not Notch2 Is Essential for Generating Hematopoietic Stem Cells from Endothelial Cells," Immunity, vol. 18, No. 5, 2003, pp. 699-711.
Lengerke and Daley, "Autologous blood cell therapies from pluripotent stem cells," Blood Rev., vol. 24, No. 1, 2010, pp. 27-37.

Mahmood, et al., "Enhanced Differentiation of Human Embryonic Stem Cells to Mesenchymal Progenitors by Inhibition of TGF-B/Activin/Nodal Signaling Using SB-431542," Journal of Bone and Mineral Research, vol. 25, No. 6, 2010, pp. 1216-1233.
Nakajima-Takagi, et al, "Manipulation of Hematopoietic Stem Cells for Regenerative Medicine," The Anatomical Record, vol. 297, 2014, pp. 111-120.
Office Action dated Oct. 12, 2017 for U.S. Appl. No. 14/759,631, 10 pages.
Office Action dated Mar. 23, 2017 for U.S. Appl. No. 14/759,631, 9 pages.
Ogawa, et. al., "Activin-Nodal signaling is involved in propagation of mouse embryonic stem cells," Journal of Cell Science, vol. 120, 2007, pp. 55-65.
Ohishi, et al., "Delta-1 enhances marrow and thymus repopulating ability of human CD34(+)CD38(−) cord blood cells," J. Clin. Invest., vol. 110, No. 8, 2002, pp. 1165-1174.
Park, et al., "Hematopoietic stem cell expansion and generation: the ways to make a breakthrough," Blood Research, vol. 50, No. 4, 2015, pp. 194-203.
Petit-Cocault, et al., "Dual role of Mpl receptor during the establishment of definitive hematopoiesis," Development, vol. 134, No. 16, 2007, pp. 3031-3040.
Piacibello, et al., "Negative Influence of IL3 on the Expansion of Human Cord Blood In Vivo Long-Term Repopulating Stem Cells," J. Hematother. Stem Cell Res., vol. 9, No. 6, 2000, pp. 945-956.
Pui, et al., "Notch1 expression in early lymphopoiesis influences B versus T lineage determination," Immunity, vol. 11, No. 3, 1999, pp. 299-308.
Radtke, et al., "Deficient T Cell Fate Specification in Mice with an Induced Inactivation of Notch1," Immunity, vol. 10, No. 5, 1999, pp. 547-558.
Robey, et al., "An activated form of Notch influences the choice between CD4 and CD8 T cell lineages," Cell, vol. 87, No. 3, 1996, pp. 483-492.
Robin, et al., "The roles of BMP and IL-3 signaling pathways in the control of hematopoietic stem cells in the mouse embryo," Int. J. Dev. Biol., vol. 54, 2010, pp. 1189-1200.
Shpall, et al., "Transplantation of ex vivo expanded cord blood," Biol. Blood Marrow Transplant., vol. 8, No. 7, 2002, pp. 368-376.
Search Report and Written Opinion dated Jun. 20, 2014 in International Application No. PCT/US14/10463, 17 pages.
Takahiro, et al., "Notch signaling in hematopoietic stem cells," Int. J. Hematol., vol. 82, No. 4, 2005, pp. 285-294.
Takayama and Eto, "In Vitro Generation of Megakaryocytes and Platelets from Human Embryonic Stem Cells and nduced Pluripotent Stem Cells," Cell Mol. Life Sci., vol. 788, 2012, pp. 205-217.
Takayama and Eto, "Pluripotent stem cells reveal the developmental biology of human megakaryocytes and provide a source of platelets for clinical application," Cell Mol. Life Sci., vol. 69, 2012, pp. 3419-3428.
Takeuchi, et al., "Cultivation of aorta-gonad-mesonephros-derived hematopoietic stem cells in the fetal liver microenvironment amplifies long-term repopulating activity and enhances engraftment to the bone marrow," Blood, vol. 99, No. 4, 2002, pp. 1190-1196.
Takizawa, et al., "Ex Vivo expansion of hematopoietic stem cells: mission accomplished?" Swiss Medical Weekly, European Journal of Medical Science, 2011, 9 pages.
Tomita, et al., "The bHLH gene Hes1 is essential for expansion of early T cell precursors," Genes Dev., vol. 13, No. 9, 1999, pp. 1203-1210.
Ueda, et al., "Expansion of human NOD/SCID-repopulating cells by stem cell factor, Flk2/Flt3 ligand, thrombopoitin, IL-6, and soluable IL-6 receptor," J Clin. Invest., vol. 105, No. 7, 2000, pp. 1013-1021.
Varnum-Finney, et al., "Immobilization of Notch ligand, Delta-1, is required for induction of notch signaling," J. Cell Science, vol. 113, Part 23, 2000, pp. 4313-4318.
Varnum-Finney, et al., "Combined effects of Notch signaling and cytokines induce a multiple log increase in precursors with lymphoid and myeloid reconstituting ability," Blood, vol. 101, No. 5, 2003, pp. 1784-1789.

(56) References Cited

OTHER PUBLICATIONS

Varnum-Finney, et al., "The Notch ligand, Jagged-1, influences the development of primitive hematopoietic precursor cells," Blood, vol. 91, No. 11, 1998, pp. 4084-4991.

Walker, et al., "The Notch/Jagged pathway inhibits proliferation of human hematopoietic progenitors in vitro," Stem Cells, vol. 17, No. 3, 1999, pp. 162-171.

Wang, et al., "TGF Beta inhibition enhances the generation of hematopoietic progenitors from human ES cell-derived hemogenic endothelial cells using a stepwise strategy," Cell Res., vol. 22, No. 1, 2012, pp. 194-207.

Washburn, et al., "Notch activity influences the alphabeta versus gammadelta T cell lineage decision," Cell, vol. 88, No. 6, 1997, pp. 833-843.

Xiao, et. al., "Cellular and Molecular Aspects of Human CD34-CD38-Precurrsors: Analysis of a Primitive Hematopoietic Population," Leukemia & Lymphoma, vol. 38, No. 5-6, 2000, pp. 489-497.

Xie & Zhang, "Ex Vivo expansion of hematopoietic stem cells," Sci. China Life Sci., vol. 58, No. 9, 2015, pp. 839-853.

Zeuner, et al., "Concise Review: Stem Cell-Derived Erythrocytes as Upcoming Players in Blood Transfusion," Stem Cells, vol. 30, No. 8, 2012, pp. 1587-1596.

\* cited by examiner

COMPOSITIONS AND METHODS FOR EXPANSION OF EMBRYONIC HEMATOPOIETIC STEM CELLS

CROSS-REFERENCE TO RELATED APPLICATIONS

This application is a continuation of U.S. patent application Ser. No. 15/939,199, filed on Mar. 28, 2018, which is a continuation of U.S. patent application Ser. No. 14/759,631, filed on Jul. 7, 2015, now U.S. Pat. No. 9,956,249, which is a U.S. National Phase Patent Application based on International Patent Application No. PCT/US2014/010463, filed on Jan. 7, 2014, which claims the benefit of U.S. Provisional Patent Application No. 61/750,332, filed on Jan. 8, 2013, each of which is incorporated herein by reference in its entirety.

STATEMENT REGARDING FEDERALLY SPONSORED RESEARCH OR DEVELOPMENT

This invention was made with government support under HL206320 and CA076930 awarded by the National Institutes of Health. The government has certain rights in the invention.

FIELD OF THE INVENTION

The present invention relates to methods, kits and compositions for expansion of embryonic hematopoietic stem cells and providing hematopoietic function to human patients in need thereof. In one aspect, it relates to kits and compositions comprising a Notch agonist, one or more growth factors, and, optionally, an inhibitor of the TGFβ pathway. Also provided herein are methods for expanding embryonic hematopoietic stem cells using kits and compositions comprising a Notch agonist, one or more growth factors, and, optionally, an inhibitor of the TGFβ pathway. The embryonic hematopoietic stem cells expanded using the disclosed kits, compositions and methods include cells derived from an embryo (e.g., aorta-gonad-mesonephros region of the embryo), embryonic stem cells, induced pluripotent stem cells, or reprogrammed cells of other types. The present invention also relates to administering the embryonic hematopoietic stem cells expanded using a combination of a Notch agonist, one or more growth factors, and, optionally, an inhibitor of the TGFβ pathway to a patient for short-term and/or long-term in vivo repopulation benefits.

BACKGROUND OF THE INVENTION

Hematopoietic stem cells (HSC) have therapeutic potential as a result of their capacity to restore blood and immune cells in transplant recipients. Specifically, autologous or allogeneic transplantation of HSC can be used for the treatment of patients with inherited immunodeficient and autoimmune diseases and diverse hematopoietic disorders to reconstitute the hematopoietic cell lineages and immune system defense. Human bone marrow transplantation methods are currently used as therapies for leukemia, lymphoma, and other life-threatening diseases. For these procedures, a large number of stem cells must be isolated to ensure that there are enough HSC for engraftment. The number of HSC available for treatment is a clinical limitation. See U.S. Patent Publication No. 2010/0183564.

Prolonged pancytopenia is common following intensive chemotherapy regimens, myeloablative and reduced intensity regimens for hematopoietic cell transplantation (HCT), and exposure to acute ionizing radiation. Of particular concern is prolonged neutropenia, which results in a significant risk of infection despite improved antimicrobial therapy and increases morbidity and mortality. Thus, novel therapies that can abrogate prolonged pancytopenia/neutropenia following high dose chemotherapy and/or radiation, and potentially facilitate more rapid hematopoietic recovery, are needed.

Novel therapies that can provide gene therapy and correct inherited disorders are also needed. The novel therapies are needed to correct both genetic diseases of hematopoietic organs and genetic diseases that involve non-hematopoietic organs.

Hematopoietic Stem Cells

The hematopoietic stem cell is pluripotent and ultimately gives rise to all types of terminally differentiated blood cells. The hematopoietic stem cell can self-renew, or it can differentiate into more committed progenitor cells, which progenitor cells are irreversibly determined to be ancestors of only a few types of blood cell. For instance, the hematopoietic stem cell can differentiate into (i) myeloid progenitor cells, which myeloid progenitor cells ultimately give rise to monocytes and macrophages, neutrophils, basophils, eosinophils, erythrocytes, megakaryocytes/platelets, dendritic cells, or (ii) lymphoid progenitor cells, which lymphoid progenitor cells ultimately give rise to T-cells, B-cells, and lymphocyte-like cells called natural killer cells (NK-cells). Once the stem cell differentiates into a myeloid progenitor cell, its progeny cannot give rise to cells of the lymphoid lineage, and, similarly, lymphoid progenitor cells cannot give rise to cells of the myeloid lineage. For a general discussion of hematopoiesis and hematopoietic stem cell differentiation, see Chapter 17, Differentiated Cells and the Maintenance of Tissues, Alberts et al., 1989, Molecular Biology of the Cell, 2nd Ed., Garland Publishing, New York, N.Y.; Chapter 2 of Regenerative Medicine, Department of Health and Human Services, August 2006, and Chapter 5 of Hematopoietic Stem Cells, 2009, Stem Cell Information, Department of Health and Human Services.

In vitro and in vivo assays have been developed to characterize hematopoietic stem cells, for example, the spleen colony forming (CFU-S) assay and reconstitution assays in immune-deficient mice. Further, presence or absence of cell surface protein markers defined by monoclonal antibody recognition have been used to recognize and isolate hematopoietic stem cells. Such markers include, but are not limited to, Lin, CD34, CD38, CD43, CD45RO, CD45RA, CD59, CD90, CD109, CD117, CD133, CD166, and HLA DR, and combinations thereof. See Chapter 2 of Regenerative Medicine, Department of Health and Human Services, August 2006, and the references cited therein.

Notch Pathway

Members of the Notch family encode large transmembrane proteins that play central roles in cell-cell interactions and cell-fate decisions during early development in a number of invertebrate systems (Simpson, 1995, Nature 375: 736-7; Artavanis-Tsakonis et al., 1995, Science. 268:225-232; Simpson, 1998, Semin. Cell Dev. Biol. 9:581-2; Go et al., 1998, Development. 125:2031-2040; Artavanis-Tsakonas and Simpson, 1991, Trends Genet. 7:403-408). The Notch receptor is part of a highly conserved pathway that enables a variety of cell types to choose between alternative differentiation pathways based on those taken by immediately neighboring cells. This receptor appears to act through an undefined common step that controls the progression of uncommitted cells toward the differentiated state by inhibiting their competence to adopt one of two alternative fates, thereby allowing the cell either to delay differentiation, or in the presence of the appropriate developmental signal, to commit to differentiate along the non-inhibited pathway.

Genetic and molecular studies have led to the identification of a group of genes which define distinct elements of the Notch signaling pathway. While the identification of these various elements has come exclusively from *Drosophila* using genetic tools as the initial guide, subsequent analyses have lead to the identification of homologous proteins in vertebrate species including humans. The molecular relationships between the known Notch pathway elements as well as their subcellular localization are depicted in Artavanis-Tsakonas et al., 1995, Science 268:225-232; Artavanis-Tsakonas et al., 1999, Science 284:770-776; and in Kopan et al., 2009, Cell 137:216-233. Proteins of the Delta family and proteins of the Serrate (including Jagged, the mammalian homolog of Serrate) family are extracellular ligands of Notch. The portion of Delta and Serrate responsible for binding to Notch is called the DSL domain, which domain is located in the extracellular domain of the protein. Epidermal growth factor-like repeats (ELRs) 11 and 12 in the extracellular domain of Notch are responsible for binding to Delta, Serrate and Jagged. See Artavanis-Tsakonas et al., 1995, Science 268:225-232 and Kopan et al., 2009, Cell 137:216-233.

Notch Pathway in Hematopoiesis

Evidence of Notch-1 mRNA expression in human CD34+ precursors has led to speculation for a role for Notch signaling in hematopoiesis (Milner et al., 1994, Blood 3:2057-62). This is further supported by the demonstration that Notch-1 and -2 proteins are present in hematopoietic precursors, and, in higher amounts, in T cells, B cells, and monocytes, and by the demonstration of Jagged-1 protein in hematopoietic stroma (Ohishi et al., 2000, Blood 95:2847-2854; Varnum-Finney et al., 1998, Blood 91:4084-91; Li et al., 1998, Immunity 8:43-55).

The clearest evidence for a physiologic role of Notch signaling has come from studies of T cell development which showed that activated Notch-1 inhibited B cell maturation but permitted T cell maturation (Pui et al., 1999, Immunity 11:299-308). In contrast, inactivation of Notch-1 or inhibition of Notch-mediated signaling by knocking out HES-1 inhibited T cell development but permitted B cell maturation (Radtke et al., 1999, Immunity 10: 47-58; Tomita et al., 1999, Genes Dev. 13:1203-10). These opposing effects of Notch-1 on B and T cell development raise the possibility that Notch-1 regulates fate decisions by a common lymphoid progenitor cell.

Other studies in transgenic mice have shown that activated Notch-1 affects the proportion of cells assuming a CD4 vs. CD8 phenotype as well as an $\alpha\beta$ vs. $\gamma\delta$ cell-fate (Robey et al., 1996, Cell 87:483-92; Washburn et al., 1997, Cell 88:833-43). Although this may reflect an effect on fate decisions by a common precursor, more recent studies have suggested that these effects may result from an anti-apoptotic effect of Notch-1 that enables the survival of differentiating T cells that would otherwise die (Deftos et al., 1998, Immunity 9:777-86; Jehn et al., 1999, J Immunol. 162:635-8).

Studies have also shown that the differentiation of isolated hematopoietic precursor cells can be inhibited by ligand-induced Notch signaling. Co-culture of murine marrow precursor cells (Lin–Sca-1+c-kit+) with 3T3 cells expressing human Jagged-1 led to a 2 to 3 fold increase in the formation of primitive precursor cell populations (Varnum-Finney et al., 1998, Blood 91:4084-4991; Jones et al., 1998, Blood 92:1505-11). Incubation of sorted precursors with beads coated with the purified extracellular domain of human Jagged-1 also led to enhanced generation of precursor cells (Varnum-Finney et al., 1998, Blood 91:4084-91).

In a study of human CD34+ cells, expression of the intracellular domain of Notch-1 or exposure to cells that overexpressed Jagged-2 also led to enhanced generation of precursor cells and prolonged maintenance of CD34 expression (Carlesso et al., 1999, Blood 93:838-48). In another study, the effects of Jagged-1-expressing cells on CD34+ cells were influenced by the cytokines present in the cultures; in the absence of added growth factors, the interaction with cell-bound Jagged-1 led to maintenance of CD34+ cells in a non-proliferating, undifferentiated state, whereas the addition of c-kit ligand led to a 2-fold increase in erythroid colony-forming cells (Walker et al., 1999, Stem Cells 17:162-71).

Expansion and Engraftment of Hematopoietic Stem/Progenitor Cells

Past efforts have attempted to expand hematopoietic stem/progenitor cells (HSPC) using soluble cytokine mediated methodologies; however, these attempts have demonstrated limited clinical efficacy (see Shpall et al., 2002, Biol Blood Marrow Transplant. 8(7): 368-376; de Lima et al., 2008, Blood. 112: Abstract 154; Jaroscak et al., 2003, Blood. 101(12): 5061-5067).

Varnum-Finney et al., 1993, Blood 101:1784-1789 demonstrated that activation of endogenous Notch receptors in mouse marrow precursor cells by an immobilized Notch ligand revealed profound effects on the growth and differentiation of the precursor cells, and that a multilog increase in the number of precursor cells with short-term lymphoid and myeloid repopulating ability was observed.

Delaney et al., 2005, Blood 106:2693-2699 and Ohishi et al., 2002, J. Clin. Invest. 110:1165-1174 demonstrated that incubation of human cord blood progenitors in the presence of an immobilized Notch ligand generated an approximate 100-fold increase in the number of CD34+ cells with enhanced repopulating ability as determined in an immunodeficient mouse model. See also U.S. Pat. No. 7,399,633 B2.

Delaney et al., 2010, Nature Med. 16(2): 232-236 demonstrated that a population of CD34+ cells obtained from a frozen cord blood sample, which population had been cultured in the presence of a Notch ligand (resulting in a greater than 100 fold increase in the number of CD34+ cells), repopulated immunodeficient mice with markedly enhanced kinetics and magnitude, and provided more rapid myeloid engraftment in humans in a clinical phase 1 myeloablative cord blood transplant trial.

Expansion techniques for cord blood stem cells have been described. See, e.g., U.S. Pat. No. 7,399,633 B2 to Bernstein et al., and Delaney et al., 2010, Nature Med. 16(2): 232-236. Delaney et al. reported rapid engraftment after infusion of previously cryopreserved cord blood stem cells which had been selected on the basis of HLA matching, and which had been expanded ex vivo.

International Patent Publication No. WO 2006/047569 A2 discloses methods for expanding myeloid progenitor cells that do not typically differentiate into cells of the lymphoid lineage, and which can be MHC-mismatched with respect to the recipient of the cells.

International Patent Publication No. WO 2007/095594 A2 discloses methods for facilitating engraftment of hematopoietic stem cells by administering myeloid progenitor cells in conjunction with the hematopoietic stem cell graft, for example, where the hematopoietic stem cell graft is suboptimal because it has more than one MHC mismatch with respect to the cells of the recipient patient.

U.S. Pat. No. 5,004,681 to Boyse et al. discloses the use of human cord blood stem cells for hematopoietic reconstitution.

U.S. Patent Publication No. 2010/0183564 to Boitano et al. discloses methods and compositions for expanding HSPC populations using an agent capable of down-regulating the activity and/or expression of aryl hydrocarbon receptor and/or a downstream effector of aryl hydrocarbon receptor pathway.

International Patent Publication No. WO 2011/127470 A1 discloses methods and compositions for providing hematopoietic function to a human patient, by selecting an expanded human umbilical cord blood stem/progenitor cell sample without taking into account the HLA-type of the expanded human cord blood stem cell/progenitor sample or the HLA-type of the patient, and administering the selected expanded human cord blood stem/progenitor cell sample to the patient; as well as methods for obtaining the expanded human cord blood stem cell/progenitor cell samples; and banks of frozen expanded human cord blood stem cell/progenitor cell samples, and methods for producing such banks.

International Patent Publication No. WO 2011/127472 A1 discloses methods and compositions for providing hematopoietic function to a human patient, by selecting a pool of expanded human umbilical cord blood stem/progenitor cell samples for administration to a patient, wherein the samples in the pool collectively do not mismatch the patient at more than 2 of the HLA antigens or alleles typed in the patient, and administering the selected pool of expanded human cord blood stem/progenitor cell samples to the patient; as well as methods for obtaining the pools of expanded human cord blood stem cell/progenitor cell samples; and banks of frozen pools of expanded human umbilical cord blood stem cell/progenitor cell samples, and methods for producing such banks.

There is a need for successful expansion of embryonic hematopoietic stem cells (eHSC), such as hematopoietic stem cells from embryonic sources, embryonic stem cells (ESC), induced pluripotent stem cells (iPSC) or reprogrammed cells of other types (non-pluripotent cells reprogrammed into eHSC). In particular, there is a need for successful expansion of human embryonic hematopoietic stem cells. Specifically, there is a need for successful generation of expanded human embryonic hematopoietic stem cells capable of short and long-term multilineage engraftment. Current methods for generation of engrafting eHSC are inefficient, and unable to generate long-term engraftment in the absence of overexpressing potentially deleterious transcription factors. The only reproducible method to generate long-term multilineage engraftment from embryonic hematopoietic stem cells known to date involves overexpression of HOXB4, a potentially oncogenic transcription factor, in murine ESC/iPSC (see Lengerke & Daley, 2010, Blood Rev. 24:27-37).

Citation or identification of any reference in Section 2 or any other section of this application shall not be construed as an admission that such reference is available as prior art to the present invention.

SUMMARY OF THE INVENTION

Described herein are methods of expanding embryonic hematopoietic stem cells, comprising culturing the embryonic hematopoietic stem cells ex vivo in the presence of a composition comprising a Notch agonist and one or more growth factors, thereby producing an expanded embryonic hematopoietic stem cell sample. Also described herein are methods of expanding embryonic hematopoietic stem cells, comprising culturing the embryonic hematopoietic stem cells ex vivo in the presence of a composition comprising a Notch agonist, one or more growth factors, and an inhibitor of the TGFβ pathway, thereby producing an expanded embryonic hematopoietic stem cell sample. Further described herein are methods of expanding embryonic hematopoietic stem cells, comprising culturing the embryonic hematopoietic stem cells ex vivo in the presence of a composition comprising a Notch agonist and one or more growth factors, wherein said culturing is not in the presence of an aryl hydrocarbon receptor antagonist, thereby producing an expanded embryonic hematopoietic stem cell sample. Also described herein are methods of expanding embryonic hematopoietic stem cells, comprising culturing the embryonic hematopoietic stem cells ex vivo in the presence of a composition comprising a Notch agonist and one or more growth factors, wherein the embryonic hematopoietic stem cells are derived from induced pluripotent stem cells (iPSC) or reprogrammed non-pluripotent cells, thereby producing an expanded embryonic hematopoietic stem cell sample. In addition, described herein are compositions and kits used in the methods described above, such as those comprising a Notch agonist, one or more growth factors, and, optionally, an inhibitor of the TGFβ pathway. Further described herein is treatment of hematopoietic disorders and/or gene therapy for hematopoietic disorders using the embryonic hematopoietic stem cells expanded in accordance with the methods described herein.

Definitions

Although any methods and materials similar or equivalent to those described herein can be used in the practice or testing of the present invention, the preferred methods and materials are described. For purposes of the present invention, the following terms are defined below.

As used herein, the terms "embryonic hematopoietic stem cells" or "eHSC" mean definitive hematopoietic stem cells that are capable of engrafting a recipient of any age post-birth. Embryonic hematopoietic stem cells can be derived from: an embryo (e.g., aorta-gonad-mesonephros region of an embryo), embryonic stem cells (ESC), induced pluripotent stem cells (iPSC), or reprogrammed cells of other types (non-pluripotent cells of any type reprogrammed into eHSC). The eHSC of the invention are not fetal liver HSC, adult peripheral blood HSC or umbilical cord blood HSC. The embryonic hematopoietic stem cells can be enriched in populations of cells positive for VE-Cadherin, CD45, or a combination thereof. The eHSC are preferably human.

As used herein, the term "Enriched eHSC" refers to a cell population enriched in embryonic hematopoietic stem cells. The Enriched eHSC are preferably human.

As used herein, the term "Expanded eHSC" refers to a cell population containing eHSC that have been expanded in cell number by use of a combination of a Notch agonist, one or more growth factors, and, optionally, an inhibitor of the TGFβ pathway, according to a method of the invention as disclosed herein. Expanded eHSC are referred to interchangeably herein as "an expanded embryonic hematopoietic stem cell sample." The expansion of eHSC can be shown by an increase in the number of eHSC in an aliquot of the sample thus expanded. Expansion of the eHSC can be shown by (i) the increased ability of the expanded cell sample to provide hematopoietic engraftment of a subject post-birth; and/or (ii) an increased number of repopulating cells determined by limiting-dilution analysis as shown by enhanced engraftment in NOD/SCID or other immunodeficient (e.g., lethally irradiated) mice infused with an aliquot of the sample thus expanded; relative to that seen with an aliquot of the sample that is not subjected to the expansion method. In a specific embodiment, enhanced engraftment in NOD/SCID or other immunodeficient mice can be detected by detecting an increased percentage of human CD45+ cells in the bone marrow of mice infused with an aliquot of the expanded sample relative to mice infused with an aliquot of the sample prior to expansion, at, e.g., 2 weeks, 3 weeks, 6 weeks, 14 weeks, or 16 weeks post-infusion (e.g., see Delaney et al., 2010, Nature Med. 16(2): 232-236). Expanded eHSC may include hematopoietic stem cells capable of short-term repopulation, hematopoietic stem cells capable of long-term repopulation (the eHSCs) and hematopoietic progenitor cells. In a specific embodiment, the expansion method results in an at least 50-, 75-, 100-, 150-, 200-, 250-, 300-, 350-, 400-, 450-, or 500-fold increase in the number of eHSC in an aliquot of the sample expanded.

As used herein, the term "Delta" refers to any of the proteins or genes, as the case may be, of the *Drosophila* Delta family or its mammalian homolog Delta (also known as "Delta-like") family. Proteins or genes of the Delta family, as the case may be, include, but are not limited to, Delta-1 (where mammalian Delta-1 is also known as Delta-like 1), Delta-3 (where mammalian Delta-3 is also known as Delta-like 3), and Delta-4 (where mammalian Delta-4 is also known as Delta-like 4).

As used herein, the term "Serrate" refers to any of the proteins or genes, as the case may be, of the *Drosophila* Serrate family or its mammalian homolog, Jagged, family.

As used herein, the term "Jagged" refers to any of the proteins or genes, as the case may be, of the Jagged family such as, but not limited to, Jagged-1 and Jagged-2.

Deltaext-IgG and DeltaExt-IgG are used interchangeably herein.

Delta1ext-IgG and Delta1Ext-IgG are used interchangeably herein.

As used herein, the term "an aryl hydrocarbon receptor antagonist" refers to any of the aryl hydrocarbon receptor antagonists described in U.S. Patent Publication No. 2010/0183564, the disclosure of which is incorporated by reference herein.

BRIEF DESCRIPTION OF THE DRAWINGS

(FIG. 2C) and (FIG. 2D) show long-term, multilineage hematopoietic reconstitution capacity of expanded cells transplanted into irradiated adult mice.

(FIG. 3C) A representative experiment showing cells and colonyforming progenitors (CFU) generated in experiments with SB431542 or control (DMSO).

(FIG. 4B) AGM-derived HSPC expanded on Notch ligand Delta1$^{Ext-IgG}$ maintain long-term multilineage repopulating myeloid and B/T lymphoid capacity compared to cells cultured on control hIgG, when examined at 14-16 weeks in peripheral blood of competitively transplanted mice. Data is compiled from 3 independent experiments. % Donor in Mouse was assessed using CD45 as a marker. % Donor Myeloid in Mouse was assessed using a combination of F4/80 and Gr-1.

DETAILED DESCRIPTION OF THE INVENTION

Figure 1:
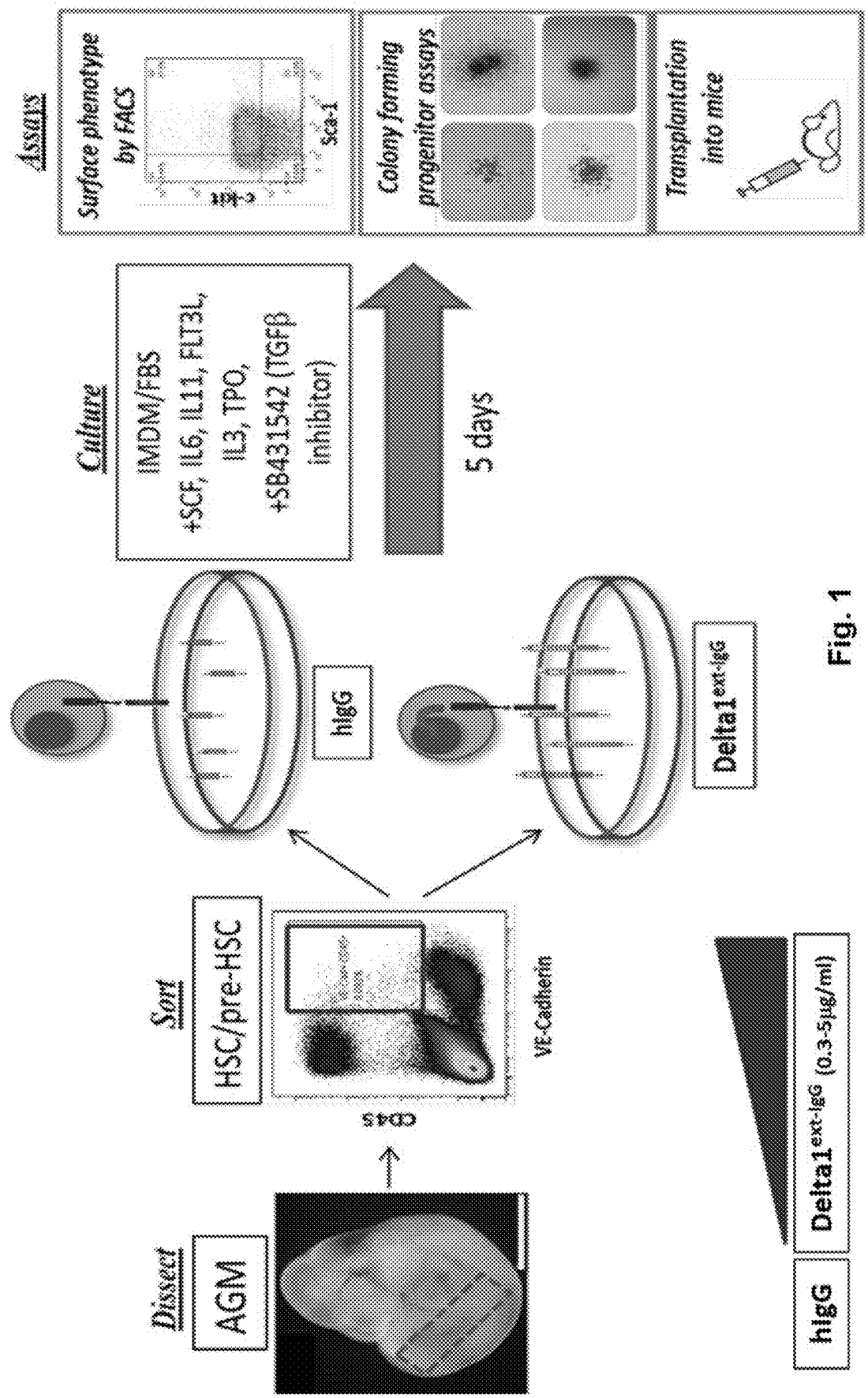
FIG. 1 shows the design of the study. The data for this study is presented in FIGS. 2A-2D. The results for surface phenotype by FACS assay are presented in FIG. 2A. The results for colony forming progenitor assays are presented in FIG. 2B. The results for transplantation into mice assays are presented in FIGS. 2C and 2D.

The present invention provides compositions, kits and methods for expanding embryonic hematopoietic stem cells, and providing hematopoietic function and/or gene therapy to a human patient of any age post-birth in need thereof by administering the expanded embryonic hematopoietic stem cells to the patient. In particular, the present invention relates to compositions and kits comprising a Notch agonist in combination with one or more growth factors, methods for expanding embryonic hematopoietic stem cells using such compositions and kits, and methods for providing hematopoietic function (such as short-term and/or long-term multilineage engraftment) and/or gene therapy to human patients in need thereof using such expanded embryonic hematopoietic stem cells. Optionally, the compositions and kits of the invention comprising Notch agonist and one or more growth factors, further comprise an inhibitor of the TGFβ pathway (such as SB431542). Accordingly, in some embodiments, the present invention relates to compositions and kits comprising a Notch agonist in combination with one or more growth factors and an inhibitor of the TGFβ pathway, methods for expanding embryonic hematopoietic stem cells using such compositions and kits, and methods for providing hematopoietic function (such as short-term and/or long-term multilineage engraftment) and/or gene therapy to human patients in need thereof using such expanded embryonic hematopoietic stem cells.

The inventors of the present invention have unexpectedly found that a Notch agonist (e.g., Delta1 or Jagged1), in the presence of one or more growth factors, is able to expand embryonic hematopoietic stem cells (eHSC). The inventors have further found that, surprisingly, combining a Notch agonist (such as Delta1ext-IgG) and one or more growth factors with an inhibitor of the TGFβ pathway (such as SB431542) results in an additive and/or synergistic effect on expansion of the eHSC. Further, the inventors have discovered that a Notch agonist (such as Delta1ext-IgG) in the presence of one or more growth factors and, optionally, in combination with an inhibitor of the TGFβ pathway (such as SB431542), promotes expansion of progenitors with erythromyeloid colony forming potential and T/B-lymphoid potential in vitro, with concurrent maturation of surface phenotype to that resembling fetal liver-stage HSC.

Furthermore, unexpectedly, the data obtained by the inventors and presented herein (see Section 7, Example) show that use of a Notch agonist (e.g., Delta1 or Jagged1) for expansion of eHSC mediates expansion of cells that demonstrate rapidly engrafting myeloid and lymphoid capacity and capacity for long-term multilineage engraftment when administered to a patient of any age post-birth. In addition, the data obtained by the inventors and presented herein suggest that, surprisingly, combining a Notch agonist (such as Delta1ext-IgG) and one or more growth factors with an inhibitor of the TGFβ pathway (such as SB431542) results in an additive and/or synergistic effect on expansion of cells that demonstrate rapidly engrafting myeloid and lymphoid capacity and capacity for long-term multilineage engraftment when administered to a patient of any age post-birth.

Infusion of the Expanded eHSC of the invention can provide a therapeutic benefit for patients with immunodeficient and autoimmune diseases, diverse hematopoietic disorders (including genetic hematopoietic disorders), non-hematopoietic genetic disorders that can be corrected by transplantation of hematopoietic stem cells carrying a normal gene (e.g., carrying a gene from a wild-type donor or a gene corrected by methods described herein or known in the art), or those who had undergone chemotherapy. The use of chemotherapeutic agents can be immunosuppressive and/or highly myelosuppressive, leading to prolonged neutropenia, often resulting in frequent infections in treated patients. In some aspects of the invention, the infusion of eHSC expanded in accordance with the methods described herein abrogates or ameliorates neutropenia in a patient. In one aspect, the Expanded eHSC of the invention abrogate or ameliorate neutropenia resulting from chemotherapy, preventing infectious complications, and facilitating host hematopoietic recovery post-chemotherapy. In other aspects, the Expanded eHSC of the invention can be used in gene therapy for hematopoietic disorders or non-hematopoietic disorders. In particular, the eHSC expanded in accordance with the methods described herein can be derived from ESC, iPSC or reprogrammed cells of other types (reprogrammed into eHSC) obtained from a patient suffering from a hematopoietic disorder and genetically modified to correct the hematopoietic disorder by correcting a defective gene sequence in the ESC, iPSC or reprogrammed cells, or eHSC derived from any of the foregoing, e.g., prior to expansion. Such gene-corrected and expanded eHSC can be administered to the patient suffering from the hematopoietic disorder for therapeutic hematopoietic stem cell transplantation and gene therapy. In yet another example, the eHSC expanded in accordance with the methods described herein can be derived from ESC, iPSC or reprogrammed cells of other types (reprogrammed into eHSC) obtained from a patient suffering from a non-hematopoietic disorder and genetically modified to correct the non-hematopoietic disorder by correcting a defective gene sequence in the ESC, iPSC or reprogrammed cells, or eHSC derived from any of the foregoing, e.g., prior to expansion. In some embodiments, non-hematopoietic disorders can be treated using such gene-corrected and expanded eHSC when eHSC can be delivered to the organ(s) affected by such non-hematopoietic disorders, e.g., by access to such organs via the circulatory system. In some embodiments, a non-hematopoietic disorder can be corrected by administration of such gene-corrected eHSC to the patient suffering from the non-hematopoietic disorder.

Notch Agonists

The present invention contemplates use of a Notch agonist. Contemplated for use in the present invention are any of the Notch agonists disclosed in U.S. Pat. No. 7,399,633, incorporated by reference herein in its entirety, or any other Notch agonists known in the art (also, the disclosure of Notch agonists in sec. 5.1 of U.S. Pat. No. 7,399,633 is specifically incorporated herein by reference in its entirety). The description of Notch agonists provided herein is largely found in sec. 5.1 of U.S. Pat. No. 7,399,633.

A Notch agonist is an agent that promotes, i.e., causes or increases, activation of Notch pathway function. As used herein, "Notch pathway function" shall mean a function mediated by the Notch signaling (signal transduction) pathway, including but not limited to nuclear translocation of the intracellular domain of Notch, nuclear translocation of RBP-Jκ or its *Drosophila* homolog Suppressor of Hairless; activation of bHLH genes of the Enhancer of Split complex, e.g., Mastermind; activation of the HES-1 gene or the KBF2 (also called CBF1) gene; inhibition of *Drosophila* neuroblast segregation; and binding of Notch to a Delta protein, a Jagged/Serrate protein, Fringe, Deltex or RBP-Jκ/Suppressor of Hairless, or homologs or analogs thereof. See generally the review article by Kopan et al., 2009, Cell 137:216-233 for a discussion of the Notch signal transduction pathway and its effects upon activation; see also Jarriault et al., 1998, Mol. Cell. Biol. 18:7423-7431.

Notch activation is carried out by exposing a cell to a Notch agonist. The agonist of Notch can be but is not limited to a soluble molecule, a molecule that is recombinantly expressed on a cell-surface, a molecule on a cell monolayer to which the eHSC are exposed, or a molecule immobilized on a solid phase. Exemplary Notch agonists are the extracellular binding ligands Delta and Serrate (e.g., Jagged) which bind to the extracellular domain of Notch and activate Notch signal transduction, or a fragment (e.g., the extracellular domain) of Delta or Serrate (e.g., Jagged) that binds to the extracellular domain of Notch and activates Notch signal transduction. Nucleic acid and amino acid sequences of Delta family members and Serrate family members (e.g., Jagged family members) have been isolated from several species, including human, are known in the art, and are disclosed in International Patent Publication Nos. WO 93/12141, WO 96/27610, WO 97/01571, Gray et al., 1999, Am. J. Path. 154:785-794. Jagged is a mammalian homologue of Serrate. As used in this application, Serrate shall encompass Jagged unless the context indicates otherwise.

In a specific embodiment, the Notch agonist is an extracellular domain of a Delta protein or a Serrate (e.g., Jagged) protein, or a Notch-binding region thereof, fused to a different protein (a fusion partner). The Notch agonist is preferably immobilized on a solid support. In certain embodiments, the Notch agonist is an immobilized fragment of a Delta or a Serrate (e.g., Jagged) protein consisting of the extracellular domain of the protein fused to a myc epitope tag (Deltaext-myc or Serrateext-myc, respectively) or an immobilized fragment of a Delta or a Serrate (e.g., Jagged) protein consisting of the extracellular domain of the protein fused to the Fc portion of IgG (Deltaext-IgG or Serrateext- IgG, respectively). In preferred embodiments, the Notch agonist is an immobilized fragment of a Delta or a Serrate (e.g., Jagged) protein consisting of the extracellular domain of the Delta or Serrate fused to the Fc domain of human IgG1. In preferred embodiments, a Delta protein is a human or rodent Delta protein, and a Serrate or Jagged protein is a human or rodent Jagged protein.

Notch agonists of the present invention include but are not limited to Notch proteins and analogs and derivatives (including fragments) thereof; proteins that are other elements of the Notch pathway and analogs and derivatives (including fragments) thereof; activating antibodies thereto and fragments or other derivatives of such antibodies containing the binding region thereof; nucleic acids encoding the proteins and derivatives or analogs; as well as proteins and derivatives and analogs thereof which bind to or otherwise interact with Notch proteins or other proteins in the Notch pathway such that Notch pathway activity is promoted. Such agonists include but are not limited to Notch proteins and derivatives thereof comprising the intracellular domain, Notch nucleic acids encoding the foregoing, and proteins comprising the Notch-interacting domain of Notch ligands (e.g., the extracellular domain of Delta or Serrate). Other agonists include but are not limited to RBPJκ/Suppressor of Hairless or Deltex. Fringe can be used to enhance Notch activity, for example in conjunction with Delta protein. These proteins, fragments and derivatives thereof can be recombinantly expressed and isolated or can be chemically synthesized. In certain embodiments, an immobilized antibody to a Notch protein is used as an agonist of Notch (see Wu et al., 2010, Nature 464:1052-57 for antibodies to Notch proteins).

In another specific embodiment, the Notch agonist is a cell which recombinantly expresses a protein or fragment or derivative thereof, which agonizes Notch. The cell expresses the Notch agonist in such a manner that it is made available to eHSC in which Notch signal transduction is to be activated, e.g., it is secreted, expressed on the cell surface, etc.

In yet another specific embodiment, the agonist of Notch is a peptidomimetic or peptide analog or organic molecule that binds to a member of the Notch signaling pathway. Such an agonist can be identified by binding assays selected from those known in the art, for example the cell aggregation assays described in Rebay et al., 1991, Cell 67:687-699 and in International Patent Publication No. WO 92/19734.

In a preferred embodiment the agonist is a protein consisting of at least a fragment of a protein encoded by a Notch-interacting gene which mediates binding to a Notch protein or a fragment of Notch, which fragment of Notch contains the region of Notch responsible for binding to the agonist protein, e.g., epidermal growth factor-like repeats 11 and 12 of Notch. Notch interacting genes, as used herein, shall mean the genes Notch, Delta, Serrate, Jagged, RBPJκ, Suppressor of Hairless and Deltex, as well as other members of the Delta/Serrate family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g., in *Drosophila*). Exemplary fragments of Notch-binding proteins containing the region responsible for binding to Notch are described in U.S. Pat. Nos. 5,648,464; 5,849,869; and 5,856,441.

The Notch agonists utilized by the methods of the invention can be obtained commercially, produced by recombinant expression, or chemically synthesized.

In a specific embodiment, the Notch agonist is a dominant active mutant of a Notch protein (e.g., a Notch receptor lacking the extracellular, ligand binding domain). In another embodiment, the Notch agonist is not a dominant active mutant of a Notch protein.

In some embodiments, the Notch agonist is recombinantly expressed from a nucleic acid introduced into the eHSC. Methods that can be used for recombinantly expressing a Notch agonist are described in sec. 5.3 of U.S. Pat. No. 7,399,633, which is specifically incorporated by reference herein in its entirety. In particular embodiments, the Notch agonist is a Notch protein (e.g., human or murine Notch-1, Notch-2, Notch-3 or Notch-4) consisting essentially of the intracellular domain of the Notch protein expressed recombinantly in eHSC. In specific embodiments, the recombinantly expressed Notch agonist is a chimeric Notch protein which comprises the intracellular domain of Notch receptor and the extracellular domain of another ligand-binding surface receptor (e.g., the EGF receptor). In such embodiments, the Notch pathway can be activated by exposure to a ligand of such another ligand-binding surface receptor (e.g., EGF). The recombinantly expressed Notch agonist can be expressed by eHSC from an inducible promoter. In certain embodiments, the expression of the nucleic acid encoding the Notch agonist is under the control of Cre/Lox system or FLP/FRT system. In one embodiment, the Notch agonist is flanked by Cre sites.

In a specific embodiment, exposure of the cells to a Notch agonist is not done by incubation with other cells recombinantly expressing a Notch ligand on the cell surface (although in other embodiments, this method can be used), but rather is by exposure to a cell-free Notch ligand, e.g., incubation with a cell-free ligand of Notch, which ligand is immobilized on the surface of a solid phase, e.g., immobilized on the surface of a tissue culture dish.

In specific embodiments, Notch activity is promoted by the binding of Notch ligands (e.g., Delta ligands, Serrate ligands) to the extracellular portion of the Notch receptor. Notch signaling appears to be triggered by the physical interaction between the extracellular domains of Notch and its ligands that are either membrane-bound on adjacent cells or immobilized on a solid surface. Full length ligands are agonists of Notch, as their expression on one cell triggers the activation of the pathway in the neighboring cell which expresses the Notch receptor. Soluble truncated Delta or Serrate (e. g., Jagged) molecules, comprising the extracellular domains of the proteins or Notch-binding portions thereof, preferably fused to a different protein, that have been immobilized on a solid surface, such as a tissue culture plate, are particularly preferred Notch pathway agonists. Such soluble proteins can be immobilized on a solid surface by an antibody or interacting protein, for example an antibody directed to an epitope tag with which a Delta or a Serrate is expressed as a fusion protein (e.g., a myc epitope tag, which is recognized by the antibody 9E10) or a protein which interacts with an epitope tag with which a Delta or a Serrate is expressed as a fusion protein (e.g., an immunoglobulin epitope tag, which is bound by Protein A). Immobilization can be by any method known in the art (see, e.g., Section 6.8).

In another specific embodiment, and as described in U.S. Pat. No. 5,780,300 to Artavanis-Tsakonas et al., Notch agonists include reagents that promote or activate cellular processes that mediate the maturation or processing steps required for the activation of Notch or a member of the Notch signaling pathway, such as the furin-like convertase required for Notch processing, Kuzbanian, the metalloprotease-disintegrin (ADAM) thought to be required for the activation of the Notch pathway upstream or parallel to Notch (Schlondorff and Blobel, 1999, J. Cell Sci. 112:3603-3617), or, more generally, cellular trafficking and processing proteins such as the rab family of GTPases required for movement between cellular compartments (for a review on Rab GTPases, see Olkkonen and Stenmark, 1997, Int. Rev. Cytol. 176:1-85). The agonist can be any molecule that increases the activity of one of the above processes, such as a nucleic acid encoding a furin, Kuzbanian or rab protein, or a fragment or derivative or dominant active mutant thereof, or a peptidomimetic or peptide analog or organic molecule that binds to and activates the function of the above proteins.

U.S. Pat. No. 5,780,300 further discloses classes of Notch agonist molecules (and methods of their identification) which can be used to activate the Notch pathway in the practice of the present invention, for example molecules that trigger the dissociation of the Notch ankyrin repeats with RBP-Jκ, thereby promoting the translocation of RBP-Jκ from the cytoplasm to the nucleus.

Growth Factors/Cytokines

The present invention contemplates use of a Notch agonist with one or more growth factors or cytokines for expansion of eHSC. eHSC are expanded by culturing the cells in the presence of an agonist of Notch function and one of more growth factors or cytokines for a given period of time. In some embodiments, eHSC are cultured in the presence of two or more growth factors. In yet another embodiment, eHSC are cultured in the presence of three or more growth factors, four or more growth factors, or five or more growth factors. When expansion of eHSC without differentiation is to be achieved, eHSC are cultured in the presence of growth factors that support growth but not differentiation. The growth factor can be any type of molecule, such as a protein or a chemical compound that promotes cellular proliferation and/or survival.

Exposing eHSC to one or more growth factors can be done prior to, concurrently with, or following exposure of the cells to a Notch agonist (and, optionally, an inhibitor of the TGFβ pathway). In some embodiments, eHSC are exposed to one or more growth factors for at least a portion of the time or the minimal culture time, most preferably the majority or all of the time, that eHSC are exposed to a Notch agonist (and, optionally, an inhibitor of the TGFβ pathway). The minimal culture time is the amount of time at which the cell would die or stop proliferating in the absence of the Notch agonist and the growth factors (e.g., 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or 25 weeks). In specific embodiments, the minimal culture time is from 4 to 5 days.

In specific exemplary embodiments, the growth factors present in the expansion medium include one or more of the following growth factors: stem cell factor (SCF), also known as the c-kit ligand or mast cell growth factor, Flt-3 ligand (Flt-3L), interleukin-6 (IL-6), interleukin-3 (IL-3), interleukin-7 (IL-7), interleukin-11 (IL-11), thrombopoietin (TPO), granulocyte-macrophage colony stimulating factor (GM-CSF), granulocyte colony stimulating factor (G-CSF), angiopoietin-like proteins (Angptls) (Angptl2, Angptl3, Angptl5, Angptl7, and Mfap4), insulin growth factor-2 (IFG-2), IGFBP2, Wnt3a, and fibroblast growth factor-1 (FGF-1). In some embodiments, the growth factors present in the expansion medium include one or more of the following growth factors: IL-1, IL-3, IL-6, IL-11, G-CSF, GM-CSF, SCF, FlT3-L, TPO, and erythropoietin.

In certain embodiments, the growth factors present in the expansion medium include one, two, three or more of the following growth factors: SCF, Flt-3L, IL-6, IL-3, TPO and IL-11. In a preferred embodiment, SCF, Flt-3L and IL-6 are used in the expansion methods provided herein. In another embodiment, SCF, Flt-3L, IL-6, IL-3, TPO and, optionally, Il-11 are used in the expansion methods provided herein.

IL-3 and TPO have been reported to play a role in embryonic HSC survival/self-renewal (see Robin et al., 2010, Int J Dev Biol 54:1189-1200; Petit-Cocault et al., 2007, Development 134:3031-3040). In some embodiments, IL-3 and/or TPO are used in the expansion methods provided herein. In other embodiments, Il-3 and/or TPO are not used in the expansion methods provided herein.

The amount of SCF, Flt-3L, IL-6, or TPO can be in the range of 5-1000 ng/ml, about 10-250 ng/ml, about 20-100 ng/ml, or about 50-100 ng/ml. In certain specific embodiments, the amount of SCF, Flt-3L, IL-6, or TPO is 10, 15, 20, 25, 30, 50, 100, 125, 150, 175, 200, 225, 250, 275, 300, 325, 350, 375, 400, 425 or 450 ng/ml. The amount of IL-3, IL-11, G-CSF, or GM-CSF can be in the range of 2-100 ng/ml, about 5-50 ng/ml, about 7.5-25 ng/ml, about 5-15 ng/ml, or about 10-15 ng/ml. In certain specific embodiments, the amount of Il-3, IL-11, G-CSF, or GM-CSF is 5, 6, 7, 8, 9, 10, 12.5, or 15 ng/ml. In one embodiment, one or more growth factors are added to eHSC in serum free medium. In another embodiment, one or more growth factors are added to eHSC in a medium comprising an amount of fetal bovine serum.

In specific embodiments, the amount of SCF can be in the range of 10-200 ng/ml (e.g., about 100 ng/ml); the amount of Flt-3L can be in the range of 10-200 ng/ml (e.g., about 100 ng/ml); the amount of IL-6 can be in the range of 10-100 ng/ml (e.g., about 100 ng/ml); the amount of 11-3 can be in the range of 0-100 ng/ml (e.g., about 100 ng/ml); the amount of TPO can be in the range of 0-100 ng/ml (e.g., about 20 ng/ml); the amount of Il-11 can be in the range of 0-10 ng/ml (e.g., about 10 ng/ml).

The amount or concentration of growth factors suitable for expanding eHSC of the present invention will depend on the activity of the growth factor preparation, and the species correspondence between the growth factors and eHSC, etc. Generally, when the growth factor(s) and eHSC are of the same species, the total amount of growth factor in the culture medium ranges from 1 ng/ml to 5 µg/ml, more preferably from 5 ng/ml to 1 µg/ml, and most preferably from about 5 ng/ml to 250 ng/ml. In one embodiment, eHSC are expanded by exposing eHSC to a Notch agonist and 50-100 ng/ml of SCF. In another embodiment, eHSC are expanded by exposing the eHSC to a Notch agonist and 50-100 ng/ml of each of SCF, Flt-3L, and IL-6. In yet another embodiment, eHSC are expanded by exposing the eHSC to a Notch agonist and 10-100 ng/ml of each of SCF, Flt-3L, IL-6, IL-3 and TPO, and, optionally, 5-10 ng/ml of IL-11.

In some embodiments, the amount or concentration of growth factors suitable for expanding eHSC of the present invention is the amount or concentration effective to promote proliferation of eHSC but substantially no differentiation of eHSC.

In a preferred embodiment for expanding eHSC, the cells are cultured in a tissue culture dish onto which an extracellular matrix protein is bound. In a preferred mode of the embodiment, the extracellular matrix protein is fibronectin (FN), or a fragment thereof. Such a fragment can be but is not limited to CH-296 (Dao et al., 1998, Blood 92(12):4612-

21) or RetroNectin® (a recombinant human fibronectin fragment) (Clontech Laboratories, Inc., Madison, Wis.). In certain embodiments to the foregoing culture conditions, fibronectin is excluded from the tissue culture dishes or is replaced by another extracellular matrix protein.

In a specific embodiment for expanding eHSC of the present invention, the cells are cultured on a plastic tissue culture dish containing immobilized Delta ligand, e.g., the extracellular domain of Delta, and fibronectin in the presence of about 10 ng/ml or about 200 ng/ml (or any range in between these values), and preferably about 50 ng/ml or 100 ng/ml, of each of SCF, Flt-3L and IL-6. In some embodiments, the eHSC are cultured further in the presence of about 5 or about 100 ng/ml of IL-3 (or any range in between these values), and preferably about 50 ng/ml or 100 ng/ml of IL-3. In some of these embodiments, the eHSC are cultured further in the presence of about 5 or about 100 ng/ml of TPO (or any range in between these values), and preferably about 20 ng/ml or 50 ng/ml of TPO. In some embodiments, the eHSC are cultured further in the presence of about 2 or about 20 ng/ml of IL-11 (or any range in between these values), and preferably about 5 ng/ml or 10 ng/ml of IL-11. In some alternative embodiments, fibronectin is excluded from the tissue culture dishes or is replaced by another extracellular matrix protein.

Where differentiation of eHSC is desired, eHSC (e.g., enriched eHSC or expanded eHSC) can be exposed to one or more growth factors that promote differentiation. The growth factors and cell culture conditions that promote differentiation are known in the art (see, e.g., U.S. Pat. No. 7,399,633 at Section 5.2 and Section 5.5, the disclosures of which are specifically incorporated by reference herein in their entireties). For example, SCF can be used in combination with GM-SCF or IL-7 to differentiate eHSC (e.g., expanded eHSC) into myeloid stem/progenitor cells or lymphoid stem/progenitor cells, respectively. In specific embodiments, eHSC can be differentiated into a lymphoid stem/progenitor cell by exposing eHSC to about 100 ng/ml of each of SCF and IL-7. In other embodiments, eHSC can be differentiated into a myeloid stem/progenitor cell by exposing eHSC to about 100 ng/ml of each of SCF and GM-SCF. In some embodiments, a retinoic acid receptor (RAR) agonist, or preferably all trans retinoic acid (ATRA) is used to promote the differentiation of eHSC (e.g., expanded eHSC). In certain embodiments, eHSC (e.g., expanded eHSC) are differentiated before engraftment/in vivo repopulation (i.e., before administration of Expanded eHSC to the patient).

The growth factors utilized by the methods of the invention can be obtained commercially, produced by recombinant expression, or chemically synthesized. For example, Flt-3L (human), IGF-1 (human), IL-6 (human and mouse), IL-11 (human), SCF (human), TPO (human and murine) can be purchased from Sigma (St. Louis, Mo.). IL-6 (human and murine), IL-7 (human and murine), and SCF (human) can be purchased from Life Technologies, Inc. (Rockville, Md.).

In other embodiments, the growth factors are produced by recombinant expression or by chemical peptide synthesis (e.g. by a peptide synthesizer). Methods that can be used for recombinantly expressing the growth factors are described in, e.g., sec. 5.3 of U.S. Pat. No. 7,399,633, which is specifically incorporated herein by reference in its entirety. Growth factor nucleic acid and peptide sequences are generally available from GenBank.

Preferably, but not necessarily, the growth factor(s) used to expand eHSC in the presence of a Notch agonist by the methods of the invention is derived from the same species as eHSC.

Inhibitors of the TGFβ Pathway

In some embodiments, in addition to the Notch agonist and one or more growth factors, the present invention also contemplates use of an inhibitor of the TGFβ pathway for expansion of eHSC. Such inhibitor may include any compound capable of down-regulating or inhibiting the activity of the TGFβ pathway disclosed herein or known in the art.

Inhibitors of the TGFβ pathway include small molecule inhibitors, monoclonal antibodies, siRNA, and antisense oligonucleotides. A review on of some of the inhibitors of the TGFβ pathway can be found in Lahn et al., 2005, Expert Opin. Investig. Drugs 14(6):629-643. Lahn et al. describes that TGFβ pathway can be inhibited at the translational level using antisense oligonucleotides, via inhibition of the ligand-receptor interaction using monoclonal antibodies, and via inhibition of the receptor-mediated signaling cascade using inhibitors of TGF-βRI kinases (Lahn et al., 2005).

In certain embodiments, the inhibitor of the TGFβ pathway used in the methods described herein is a small molecule inhibitor, a monoclonal antibody, an siRNA, or an antisense oligonucleotide, that causes inhibition of the TGFβ pathway. In one embodiment, the inhibitor of the TGFβ pathway used in the methods described herein is a small molecule inhibitor. In a specific embodiment, the inhibitor of the TGFβ pathway is SB431541.

SB431542 is a small molecule inhibitor of the TGFβ pathway developed by GlaxoSmithKline. Its chemical name is 4-[4-(1,3-benzodioxol-5-yl)-5-(2-pyridinyl)-1H-imidazol-2-yl]benzamide, and it has the following formula:

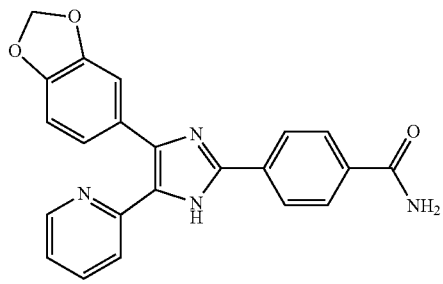 [SMILES: NC(=O)c1ccc(-c2nc(-c3ccc4c(c3)OCO4)c(-c3ccccn3)[nH]2)cc1]

SB431542 is a potent and selective inhibitor of the transforming growth factor-β (TGF-β) type I receptor activin receptor-like kinase ALK5 (1050=94 nM), and its relatives ALK4 and ALK7. SB431542 is known to suppress TGF-β-induced proliferation of human osteosarcoma cells. It is also known to stimulate proliferation, differentiation and sheet formation of ESC-derived endothelial cells. SB431542 has been shown to enhance general hematopoiesis, though not engrafting HSC, from human ESC (Wang C, et al. Cell Res. 2012 January; 22(1):194-207).

In another embodiment, the inhibitor of the TGFβ pathway used in the methods described herein is a monoclonal antibody. In yet another embodiment, the inhibitor of the TGFβ pathway used in the methods described herein is an siRNA. In yet another embodiment, the inhibitor of the TGFβ pathway used in the methods described herein is an antisense oligonucleotide.

In specific embodiments, the inhibitor of the TGFβ pathway is an antibody (e.g., monoclonal antibody) to TGFβ, an siRNA to a nucleic acid of TGFβ, or a small molecule inhibitor of TGFβ.

In certain embodiments, exposing eHSC to an inhibitor of the TGFβ pathway can be done prior to, concurrently with, or following exposure of the cells to a Notch agonist. In one embodiment, eHSC are exposed to both a Notch agonist and an inhibitor of the TGFβ pathway for the entire period of ex vivo expansion of eHSC. In some embodiments, eHSC are exposed to both a Notch agonist and an inhibitor of the TGFβ pathway for more than 80%, 85%, 90%, 95%, 98%, or 99% of the period of ex vivo expansion of eHSC. In another embodiment, eHSC are exposed to a Notch agonist and/or an inhibitor of the TGFβ pathway for less than the entire period of ex vivo expansion of eHSC. In yet another embodiment, eHSC are exposed to a Notch agonist for the entire period of ex vivo expansion of eHSC, but are exposed to an inhibitor of the TGFβ pathway for less than the entire period of ex vivo expansion (e.g., for less than 100%, 99%, 98%, 95%, 90%, 85%, 80%, 75%, 70%, 60%, or 50% of the ex vivo expansion period).

Embryonic Hematopoietic Stem Cells

Sources of eHSC include hematopoietic stem cells derived from an embryo (e.g., the aorta-gonad-mesonephros region of an embryo), embryonic stem cells (ESC), induced pluripotent stem cells (iPSC), and reprogrammed cells of other types (non-pluripotent cells of any type reprogrammed into eHSC).

eHSC can be collected from any species, including without limitation, any vertebrate, preferably any mammal (such as a human, a primate, a mouse, a rat, a rabbit, a guinea pig, a dog, a cat, a horse, a cow, a pig, a sheep, a goat, etc.). In a preferred embodiment, eHSC are collected from one or more humans. In one embodiment, eHSC are obtained from a tissue of a patient to whom they are to be administered after expansion (and, optionally, differentiation).

Methods that can be used for derivation and/or collection of eHSC from any of the sources can be any of the methods described herein or known in the art (see Ivanovs et al., 2011, J Exp Med 208:2417-2427; Lengerke & Daley, 2010, Blood Rev. 24:27-37; McKinney-Freeman et al., 2012, Cell Stem Cell 11:701-714; Rafii et al, 2012, Blood; Peters et al., 2010, Int J Dev Biol 54:965-990; Togarrati & Suknuntha, 2012, Int J Hematol 95:617-623; Amabile et al., 2013, Blood 121 (DOI:10.1182/blood-2012-06-434407); Park et al., 2013, Cytometry Part A 83A:114-126; and Yamanaka, 2012, Cell Stem Cell 10:678-684).

Embryonic hematopoietic stem cells can be derived from an embryo (e.g., the aorta-gonad-mesonephros region of an embryo) as described in Ivanovs et al., 2011, J Exp Med 208:2417-2427; Lengerke & Daley, 2010, Blood Rev. 24:27-37; or McKinney-Freeman et al., 2012, Cell Stem Cell 11:701-714.

Embryonic hematopoietic stem cells can be derived from embryonic stem cells (ESC) as described in Rafii et al, 2012, Blood; Peters et al., 2010, Int J Dev Biol 54:965-990; Lengerke & Daley, 2010, Blood Rev. 24:27-37; McKinney-Freeman et al., 2012, Cell Stem Cell 11:701-714; or Togarrati & Suknuntha, 2012, Int J Hematol 95:617-623.

Embryonic hematopoietic stem cells can be derived from induced pluripotent stem cells (iPSC) as described in Amabile et al., 2013, Blood 121 (DOI:10.1182/blood-2012-06-434407); Park et al., 2013, Cytometry Part A 83A:114-126; Togarrati & Suknuntha, 2012, Int J Hematol 95:617-623; Lengerke & Daley, 2010, Blood Rev. 24:27-37; Yamanaka, 2012, Cell Stem Cell 10:678-684; or Peters et al., 2010, Int J Dev Biol 54:965-990.

Embryonic hematopoietic stem cells can be derived from reprogrammed cells of other types (non-pluripotent cells of any type reprogrammed into eHSC) as described in Szabo et al., 2010, Nature 468:521-526; or Lengerke & Daley, 2010, Blood Rev. 24:27-37.

In a preferred embodiment, eHSC used in the methods described herein have not been obtained by recombinant expression of one or more transcription factors. In a specific embodiment, eHSC used in the methods described herein have not been obtained by recombinant expression of Cdx4/HoxB4.

In one embodiment, one or more eHSC samples (such as samples from the same embryo or the same patient) can be pooled prior to enriching for eHSC, prior to expansion of eHSC, and/or prior to engraftment of the expanded eHSC. In another embodiment, one or more eHSC samples (such as samples from the same embryo or the same patient) can be pooled after enriching for eHSC, and/or after expansion of such eHSC. In another embodiment, eHSC is not pooled.

In certain embodiments, the HLA type of eHSC sample or samples is assessed, and eHSC sample or samples selected for administration to a patient do not mismatch the HLA antigens or alleles typed in the patient (or do not mismatch the patient at more than 1 or 2 of the HLA antigens or alleles typed in the patient). In other embodiments, the eHSC sample or samples are for administration to a patient without regard to the HLA type of the eHSC or without HLA matching. In a specific embodiment, the Expanded eHSC are administered to a patient without regard to the HLA type of the eHSC or without HLA matching.

In some embodiments, wherein eHSC are derived from ESC or iPSC, the ESC or iPSC can be genetically engineered to alter HLA as needed for specific applications (e.g. to match HLA of the patient to whom the Expanded eHSC are to be administered). Since the ESC and iPSC represent an essentially limitless source of starting cells, eHSC can be generated from a single starting cell line of ESC or iPSC (which precludes the need to pool samples from multiple cell lines). In some embodiments, samples from a single ESC or a single iPSC are pooled before expansion (e.g., in order to obtain sufficient HSC suitable for expansion protocol).

In certain embodiments, eHSC used in the methods described herein are capable of generation of long-term repopulating cells when administered to a patient after expansion in the presence of a Notch agonist and an inhibitor of the TGFβ pathway (such as SB431542).

Enrichment of eHSC

Once eHSC are isolated or collected, the blood is processed to produce an enriched embryonic hematopoietic stem cell population.

The eHSC can be positive for a specific marker expressed in increased levels on the eHSC cells relative to other types of hematopoietic cells. For example, such markers can be, but are not limited to, CD 45, VE-Cadherin, CD41, CD49f, sca-1 (mouse), CD34, CD43, CD45RO, CD45RA, CD59, CD90, CD109, CD117, CD133, CD166, HLA DR, or a combination thereof. The hematopoietic stem/progenitor cells also can be negative for a specific marker relative to other types of hematopoietic cells.

eHSC can be found in the population of cells enriched in CD45 and/or VE-Cadherin. In particular, eHSC can be found in the population of cells enriched in CD45 and/or VE-Cadherin in the AGM region of an embryo; such cell population can be suitable for expansion and use of eHSC as described herein even though eHSC may constitute a small fraction of such cell population. Preferably, eHSC are CD45+ cells and/or VE-Cadherin+.

In certain embodiments, prior to processing for enrichment, the collected eHSC sample (derived, e.g., an embryo such as the AGM region of the embryo, ESC, iPSC, or reprogrammed cells) is fresh and has not been previously cryopreserved. In other embodiments, prior to processing for enrichment, the collected eHSC sample has been cryopreserved and thawed.

Any technique known in the art for cell separation/selection can be used to carry out the enrichment for hematopoietic stem/progenitor cells. For example, methods which rely on differential expression of cell surface markers can be used. For example, cells expressing the cell surface marker CD45 can be positively selected using a monoclonal antibody to CD45, such that cells expressing CD45 are retained, and cells not expressing CD45 are not retained. Moreover, the separation techniques employed should maximize the viability of the cell to be selected. The particular technique employed will depend upon efficiency of separation, cytotoxicity of the methodology, ease and speed of performance, and necessity for sophisticated equipment and/or technical skill.

Procedures for separation may include magnetic separation, using antibody-coated magnetic beads; fluorescence activated cell sorting (FACS); affinity chromatography; cytotoxic agents joined to a monoclonal antibody or used in conjunction with a monoclonal antibody, e.g., complement and cytotoxins; and "panning" with antibody attached to a solid matrix, e.g., plate, or other convenient technique. Techniques providing accurate separation/selection include fluorescence activated cell sorters, which can have varying degrees of sophistication, e.g., a plurality of color channels, low angle and obtuse light scattering detecting channels, impedance channels, etc.

The antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

In one embodiment, the enrichment of eHSC is affected by contacting an eHSC sample with a solid substrate (e.g., beads, flask, magnetic particles) to which antibodies are bound, and by removing any unbound cells, wherein the Enriched eHSC can be found either in the cells bound to the solid substrate or in the unbound cells depending on the antibodies used.

In one embodiment of the present invention, an eHSC sample is processed to select for, i.e., enrich for, CD45+ and/or VE-Cadherin+ cells using anti-CD45 and/or anti-VE-Cadherin+ antibodies directly or indirectly conjugated to magnetic particles in connection with a magnetic cell separator, for example, the CliniMACS® Cell Separation System (Miltenyi Biotec, Bergisch Gladbach, Germany), which employs nano-sized super-paramagnetic particles composed of iron oxide and dextran coupled to specific monoclonal antibodies. The CliniMACS® Cell Separator is a closed sterile system, outfitted with a single-use disposable tubing set. The disposable set can be used for and discarded after processing a single sample of eHSC. Similarly, CD41+ cells can be enriched using anti-CD41 antibodies. In some embodiments, an eHSC sample is processed to select for or enrich for any of the cell surface markers described herein or known in the art using flow cytometry.

The above-mentioned antibodies can be used alone or in combination with procedures such as "panning" (Broxmeyer et al., 1984, J. Clin. Invest. 73:939-953) or fluorescence activated cell-sorting (FACS) (Williams et al., 1985, J. Immunol. 135:1004; Lu et al., 1986, Blood 68(1):126-133) to isolate the cells containing surface determinants recognized by these antibodies, as described in sec. 5.4.1.1 of U.S. Pat. No. 7,399,633. eHSC can also be separated and/or enriched using selective agglutination using a lectin such as soybean (Reisner et al., 1980, Proc. Natl. Acad. Sci. U.S.A. 77:1164).

Methods of eHSC Expansion

After eHSC have been isolated according to the enrichment methods described above or other methods known in the art, the Enriched eHSC can be expanded in order to increase the number of eHSC. In less preferred embodiments, the methods described herein can be applied to eHSC without prior enrichment, or prior to enrichment.

In some embodiments, eHSC that are subjected to expansion using the methods described herein are fresh, i.e., they have not been previously cryopreserved and thawed. In other embodiments, eHSC that are subjected to expansion using the methods described herein have been cryopreserved and thawed.

Described herein are methods for expansion of eHSC (e.g., the Enriched eHSC) using a composition comprising a Notch agonist one or more growth factors. In a preferred embodiment of the present invention, eHSC are expanded by culturing the cells in the presence of an agonist of Notch function and one or more growth factors or cytokines and, optionally, an inhibitor of the TGFβ pathway, for a given period of time. In preferred embodiments, described herein are methods for expansion wherein eHSC (such as the Enriched eHSC) are cultured in the presence of a Notch agonist for 2-14 days (e.g., 2, 3, 4, 5, 6, 7, 8, 9, 10, 11, 12, 13, or 14 days); and in a more preferred embodiment for 4-7 days (e.g., 5, 6, or 7 days). In some embodiments, described herein are methods for expansion wherein eHSC (such as the Enriched eHSC) are cultured in the presence of a Notch agonist, one or more growth factors, and, optionally an inhibitor of the TGFβ pathway, for 2-14 days (e.g., 2, 3, 4, 5, 6, 7, 8, 9, 10, 11, 12, 13, or 14 days); and in a more preferred embodiment for 4-7 days (e.g., 5, 6, or 7 days).

Culturing eHSC can take place under any suitable culture medium/conditions described herein or known in the art (see, e.g., Freshney Culture of Animal Cells, Wiley-Liss, Inc., New York, N.Y. (1994)). The time in culture is a time sufficient to produce an Expanded eHSC population, as defined herein. For example, eHSC can be cultured in a medium comprising fetal bovine serum (FBS), e.g., 20% FBS in Iscove's Modified Dulbeco's Media (IMDM), in the presence of an agonist of Notch function, one or more growth factors or cytokines and, optionally, an inhibitor of the TGFβ pathway for 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, or 35 days; or, preferably, for at least 5 days. In another example, eHSC can be cultured in a serum-free medium in the presence of an agonist of Notch function, one or more growth factors or cytokines and, optionally, an inhibitor of the TGFβ pathway for 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, or 35 days; or, preferably, for at least 5 days. Optionally, at any point during the culturing period, the culture medium can be replaced with fresh medium or fresh medium can be added. In one embodiment, the fresh culture medium is added every 2, 3 or 4 days.

In one embodiment, a Notch agonist as described herein is immobilized (e.g., immobilized on a solid phase surface to which the cells are exposed during cell culturing), while the one or more growth factors are present in the cell culture medium. In certain embodiments, described herein are methods for expansion of eHSC (e.g., the Enriched eHSC) using a composition comprising a Notch agonist, one or more growth factors, and an inhibitor of the TGFβ pathway. In one embodiment, a Notch agonist as described herein is immobilized (e.g., immobilized on a solid phase surface to which the cells are exposed during cell culturing), while the one or more growth factors and the inhibitor of the TGFβ pathway are present in the cell culture medium.

In specific embodiments, the Notch agonist (e.g., an extracellular domain of a Notch ligand) is fused to a fusion partner before immobilization. The fusion partners can be, but are not limited to, an Fc domain of IgG or tags that contain antigenic determinants such as a myc tag. The fusion partner can be any protein or peptide preferably of at least six amino acids in length.

The solid phase surface on which a Notch agonist is immobilized can be any surface known in the art, e.g., the inside surface of a cell culture dish, flask, or container, or the surface of a bead, etc. The immobilization of a Notch agonist on the solid surface can be by any method known in the art, and can be covalent or noncovalent, by adsorption or cross-linking, etc. In a specific embodiment, an antibody to the fusion partner of an extracellular domain of a Notch ligand (e.g., a Delta or a Serrate protein, or a Notch-binding portion thereof) can be bound (e.g., covalently) to the solid phase surface, and then immunospecifically bound to the fusion partner. In one embodiment, the solid phase surface (e.g., an inside surface of a cell culture dish, flask, or container, or the surface of a bead) is pre-coated with an antibody to a fusion partner protein (e.g., an anti-myc where the fusion partner is a myc tag, or an anti-IgG Fc domain antibody where the fusion partner is an Fc domain of an IgG) before addition of an extracellular domain of a Notch ligand fused to the fusion partner.

Preferably, the Notch agonist (e.g., an extracellular domain of a Notch ligand) is immobilized on the inside surface of a cell culture dish, flask or another container. In specific embodiments, Deltaext-IgG (e.g., Delta1ext-IgG) or Deltaext-myc (e.g., Delta1ext-myc) is immobilized on the inside surface of a cell culture dish, flask or another container. In some embodiments, to present Deltaext-IgG (e.g., Delta1ext-IgG) or Deltaext-myc (e.g., Delta1ext-myc) in immobilized form, Deltaext-IgG or Deltaext-myc is attached to the surface of the cell culture dish by binding to an anti-myc tag antibody (e.g., 9E10), or anti-human IgG Fc domain antibody, respectively, that had previously been adsorbed to the surface of the cell culture dish. In other specific embodiments, Jaggedext-IgG (e.g., Jagged1ext-IgG) or Jaggedext-myc (e.g., Jagged1ext-myc) is immobilized on the inside surface of a cell culture dish, flask or another container. In some embodiments, to present Jaggedext-IgG (e.g., Jagged1ext-IgG) or Jaggedext-myc (e.g., Jagged1ext-myc) in immobilized form, Jaggedext-IgG or Jaggedext-myc is attached to the surface of the cell culture dish by binding to an anti-myc tag antibody (e.g., 9E10), or anti-human IgG Fc domain antibody, respectively, that had previously been adsorbed to the surface of the cell culture dish.

In a specific embodiment, a Notch agonist (e.g., an extracellular domain of a Notch ligand) is immobilized on beads (e.g., Sepharose beads, agarose beads, or another type of bead known in the art). A Notch agonist can be attached to the beads utilizing any methodology known in the art including, but not limited to, cross-linking, binding via antibody, or sticking. For example, an extracellular domain of a Notch ligand can be fused to a myc tag and bound to Sepharose beads crosslinked to an anti-myc tag antibody (e.g., 9E10) (see, e.g., methodology described in Varnum Finney et al., 1998, Blood 91(11):4084-4091).

In certain embodiments, a Notch agonist is any one of the compounds described in Section 6.2 above. In some embodiments, a Notch agonist is a Notch-interacting domain of a Delta (e.g., Delta-1, Delta-3 or Delta-4), a Jagged (e.g., Jagged-1 or Jagged-2), or a Serrate protein. In some embodiments, a Notch agonist comprises an extracellular domain of a Delta protein or a Serrate (e.g., Jagged) protein. In preferred embodiments, a Notch agonist comprises a human or rodent Delta protein or a human or rodent Jagged protein (e.g., an extracellular domain of a human Delta protein or a human Jagged protein). Any ligand immobilization technique known in the art can be used in the methods of the invention to immobilize the Notch agonist. In specific embodiments, a Notch agonist (e.g., an extracellular domain of a Notch ligand) is fused to a fusion partner protein. Any fusion partner protein known in the art can be used in the methods, kits and compositions of the invention. For example, a tag (with an antigenic determinant) or an intracellular domain of a receptor can be used as the fusion partner protein. Fusion partner proteins include, but are not limited to, an Fc domain of an IgG, a myc tag, and a his tag. In one embodiment, the Notch agonist is the extracellular domain of a Delta protein or a Serrate (e.g., Jagged) protein fused to the Fc domain of human IgG (e.g., Delta1ext-IgG). In another embodiment, the Notch agonist is the extracellular domain of a Delta protein or a Serrate (e.g., Jagged) protein fused to a myc epitope tag (e.g., Delta1ext-myc). Preferably, a Notch agonist (e.g., Delta1ext-IgG) is immobilized on the surface of the tissue culture dish during eHSC expansion. In specific embodiments, a Notch agonist (e.g., Delta1ext-IgG) is immobilized on beads (e.g., Sepharose beads, agarose beads, or other types of beads known in the art). In some embodiments, a Notch agonist is an immobilized antibody to a Notch protein (that activates the Notch pathway). In such embodiments, an antibody to a Notch protein can be immobilized using any method described herein or known in the art (e.g., on a solid surface or on beads). Anti-Notch antibodies are described in Wu et al., 2010, Nature 464:1052-1057.

In preferred embodiments, the one or more growth factors used in the methods of eHSC expansion provided herein is any one of the growth factors described in Section 6.2 above. In certain embodiments, the one or more growth factors can be selected from the following human growth factors: stem cell factor (SCF), Flt-3-ligand (Flt-3L), interleukin-6 (IL-6), thrombopoietin TPO, interleukin-3 (IL-3), interleukin-11 (IL-11), Angiopoietin-like 3, Angiopoietin-like 5, IGFBP2, Wnt3a. In some embodiments, eHSC (e.g., the Enriched eHSC) are expanded in the presence of two, three, four or more growth factors (such as any combination of two, three, four or more growth factors listed above). In one embodiment, the following three human growth factors are present during eHSC expansion: SCF, Flt-3L and IL-6. In one embodiment, the following five human growth factors are present during eHSC expansion: SCF, Flt-3L, IL-6, IL-3 and TPO. In one embodiment, the following six human growth factors are present during eHSC expansion: SCF, Flt-3L, IL-6, IL-3, TPO and IL-11.

In preferred embodiments, an inhibitor of the TGFβ pathway is any one of the inhibitors described in Section 6.3 above. In one embodiment, an inhibitor of the TGFβ pathway is SB431542.

In specific embodiments, described herein are methods for expansion of eHSC (e.g., the Enriched eHSC) using a composition comprising a Notch agonist, one or more growth factors, an inhibitor of the TGFβ pathway (such as SB431542) and an immobilized fibronectin or a fragment thereof. In one embodiment, an immobilized fibronectin or a fragment thereof is CH-296 or RetroNectin® (a recombinant human fibronectin fragment).

Preferably, eHSC (e.g., the Enriched eHSC) are cultured under cell growth conditions (e.g., promoting mitosis) such that the eHSC grow and divide (proliferate) to obtain a population of Expanded eHSC. In preferred embodiments, eHSC (e.g., the Enriched eHSC) used for ex vivo expansion are derived from a single patient or a single embryo (e.g., human). In some embodiments, samples of eHSC or samples of the Expanded eHSC (such as eHSC derived from a single patient or a single embryo) are pooled prior or after the expansion methods described herein. In another embodiment, the sample that is expanded is not a pool of eHSC samples.

Preferably, the technique used for expansion is one that has been shown to result in an increase in the number of eHSC in the expanded sample relative to the unexpanded eHSC sample. For example, it can be shown to result in an increased number of SCID repopulating cells in the expanded sample determined by limiting-dilution analysis as shown by enhanced engraftment in NOD/SCID mice infused with the expanded sample, relative to that seen with the unexpanded sample, where the unexpanded sample and expanded sample are from different aliquots of the same sample, wherein the expanded sample but not the unexpanded sample is subjected to the expansion technique.

In certain embodiments, the technique results in (or more than) a 50-, 75-, 100-, 150-, 200-, 250-, 300-, 350-, 400-, 450-, 500-, 1000-, 2000-, 3000-, 4000-, 5000-fold increase in the number of eHSC in the expanded sample, relative to the unexpanded sample. The Expanded eHSC can be positive for one or more of CD34, CD43, CD45RO, CD45RA, CD59, CD90, CD109, CD117, CD133, CD166, and HLA DR. In a specific embodiment, the enhanced engraftment can be detected by detecting an increased percentage of human CD45+ cells in the bone marrow of mice infused with an aliquot of the expanded sample relative to mice infused with an aliquot of the unexpanded sample at, e.g., 10 days, 2 weeks, 3 weeks, 6 weeks, 9 weeks, 14 weeks or 16 weeks post-infusion (see Delaney et al., 2010, Nature Med. 16(2): 232-236).

In one embodiment of the invention, eHSC (e.g., the Enriched eHSC) are cultured with a Notch agonist, one or more growth factors, and, optionally, an inhibitor of the TGFβ pathway, are exposed to cell growth conditions (e.g., promoting mitosis) such that the eHSC proliferate to obtain an Expanded eHSC population according to the present invention. In certain embodiments of the invention, eHSC (e.g., the Enriched eHSC) are cultured with an amount of an agonist of Notch function, an amount of one or more growth factors, and, optionally, an amount of an inhibitor of the TGFβ pathway, where the amounts of these agents together are effective to expand eHSC. In one embodiment of the invention, eHSC (e.g., the Enriched eHSC) are cultured with an amount of an agonist of Notch function effective to inhibit differentiation, an amount of one or more growth factors, and, optionally, an amount of an inhibitor of the TGFβ pathway, and are exposed to cell growth conditions (e.g., promoting mitosis) such that the eHSC proliferate to obtain an Expanded eHSC population according to the present invention. The Expanded eHSC population so obtained can be frozen and stored for later use, for example, to provide hematopoietic function to an immunodeficient human patient. Optionally, the Notch pathway agonist and/or an inhibitor of the TGFβ pathway is/are inactivated, removed or washed away from the Expanded eHSC population prior to transplantation into the patient.

In specific embodiments, eHSC (e.g., the Enriched eHSC) are cultured for 2, 3, 4, 5, 6, 7, 8, 9, 10, 11, 12, 13, 14, 15, 16, 17, 18, 19, 20, 21, 22, 23, 24, 25, or 30 days or more; or, preferably, the eHSC are cultured for at least 4 days (in the presence of the combination of a Notch agonist, one or more growth factors, and, optionally an inhibitor of the TGFβ pathway). In other embodiments, eHSC (e.g., the Enriched eHSC) are cultured for 2 to 14 days or 4 to 7 days, e.g., 4, 5, 6, or 7 days (in the presence of the combination of a Notch agonist, one or more growth factors, and, optionally an inhibitor of the TGFβ pathway). In yet other embodiments, eHSC (e.g., the Enriched eHSC) are cultured for less than 14 days (in the presence of the combination of a Notch agonist, one or more growth factors, and, optionally an inhibitor of the TGFβ pathway). In yet other embodiments, eHSC (e.g., the Enriched eHSC) are cultured for more than 2, 3, 4 or 5 days (in the presence of the combination of a Notch agonist, one or more growth factors, and, optionally an inhibitor of the TGFβ pathway).

Exemplary culture conditions for expanding eHSC (e.g., the Enriched eHSC) comprise, as set forth in Section 7 infra, culturing the eHSC for about 5 days or about 4-7 days in the presence of fibronectin fragments and the extracellular domain of a Delta protein fused to the Fc domain of human IgG (e.g., Delta1ext-IgG) in either an FBS-containing medium (such as IMDM/20% FBS) or a serum free medium supplemented with the following four human growth factors: stem cell factor, Flt-3L, and interleukin-6, or in the presence of the following five human growth factors: stem cell factor, Flt-3L, thrombopoietin, interleukin-6 and interleukin-3, or in the presence of SCF, TPO, Flt-3L, IL-6, IL-3 and IL-11. In some embodiments, the cell culture dishes are coated overnight at 4° C. (or for a minimum of 2 hours at 37° C.) with 0.3 to 20 µg/ml Delta1ext-IgG (e.g., 0.3, 0.5, 1, 1.25, 1.5, 2, 2.5, 3, 3.5, 4, 4.5, 5, 6, 7, 7.5, 8, 9, 10, 12, 14, 16, 18 or 20 µg/ml Delta1ext-IgG) or with 1 to 5 µg/ml Delta1ext-IgG (e.g., 1, 1.25, 1.5, 1.75, 2, 2.25, 2.5, 2.75, 3, 3.25, 3.5, 3.75, 4, 4.25, 4.5, 4.75 or 5 µg/ml Delta1ext-IgG) and 5 µg/ml RetroNectin® (a recombinant human fibronectin fragment) in phosphate buffered saline, before adding eHSC (e.g., the Enriched eHSC), one or more growth factors, and, optionally, an inhibitor of the TGFβ pathway.

In certain embodiments, eHSC (e.g., the Enriched eHSC) are expanded in the presence of a Notch agonist, preferably an immobilized Notch agonist, and in particular Deltaext-IgG (e.g., Delta1ext-IgG), at a concentration that is in the range of 0.3 to 20 µg/ml, 1 to 5 µg/ml, 1.5 to 3.5 µg/ml, 2 to 3 µg/ml, or 2.25 to 2.75 µg/ml, e.g., in a fluid applied to a solid phase surface. In some embodiments, eHSC (e.g., the Enriched eHSC) are expanded in the presence of a Notch agonist, preferably an immobilized Notch agonist, and in particular Deltaext-IgG (e.g., Delta1ext-IgG), at a concentration that is above 0.5, 1, 1.25, 1.5, 2, 2.25 or 2.5 µg/ml, or below 20, 15, 12, 10, 9, 8, 7.5, 7, 6, 5, 4, 3, or 2.5 µg/ml, e.g., in a fluid applied to a solid phase surface. In yet other embodiments, eHSC (e.g., the Enriched eHSC) are expanded in the presence of a Notch agonist, preferably an immobilized Notch agonist, and in particular Delta1ext-IgG, at a concentration between 0.5 and 10 µg/ml, between 1 and 10 µg/ml, between 1.25 and 10 µg/ml, between 1.5 and 10 µg/ml, between 1 and 7.5 µg/ml, between 1.25 and 7.5 µg/ml, between 1.5 and 7.5 µg/ml, between 1 and 5 µg/ml, between 1.25 and 5 µg/ml, between 1.5 and 5 µg/ml, between 1.5 and 3.5 µg/ml, between 1.5 and 3 µg/ml, between 2 and 3 µg/ml, between 2 and 3 µg/ml, between 1 and 6 µg/ml, between 2 and 6 µg/ml, or between 2.25 and 2.75 µg/ml, e.g., in a fluid applied to a solid phase surface. In a specific embodiment, a Notch agonist, preferably an immobilized Notch agonist, and in particular Deltaext-IgG (e.g., Delta1ext-IgG), is used for eHSC expansion at a concentration of 0.5, 1, 1.25, 1.5, 2, 2.25, 2.5, 2.75, 3, 3.25, 3.5, 4, 4.5, 5 or 7.5 µg/ml, e.g., in a fluid applied to a solid phase surface. In one embodiment, a Notch agonist, preferably an immobilized Notch agonist, and in particular Deltaext-IgG (e.g., Delta1ext-IgG), is used for eHSC expansion at a concentration of about 2.5 µg/ml, e.g., in a fluid applied to a solid phase surface.

In certain embodiments, the foregoing growth factors are present in the culture condition for expanding eHSC (e.g., the Enriched eHSC) at the following concentrations: 10-300 ng/ml or 10-200 ng/ml stem cell factor, 10-300 ng/ml or 10-200 ng/ml Flt-3 receptor ligand, 10-100 ng/ml thrombopoietin, 10-100 ng/ml interleukin-6, 10-100 ng/ml interleukin-3, and 1-10 ng/ml IL-11. In more specific embodiments, about 50, 100 or 200 ng/ml stem cell factor, about 50, 100 or 200 ng/ml of Flt-3 receptor ligand, about 20, 50 or 100 ng/ml thrombopoietin, about 50 or 100 ng/ml interleukin-6, about 10, 50 or 100 ng/ml interleukin-3, and/or about 5 or 10 ng/ml IL-11 are used.

In certain embodiments, an inhibitor of the TGFβ pathway (such as SB431542) is added to the medium in which eHSC (e.g., the Enriched eHSC) are cultured. In some embodiments, an inhibitor of the TGFβ pathway is added to the medium in which eHSC (e.g., the Enriched eHSC) are cultured during all of the feedings of the cells. In these embodiments, an inhibitor of the TGFβ pathway is present in the eHSC cell culture at all times during the eHSC expansion. In yet other embodiments, an inhibitor of the TGFβ pathway is not present in the eHSC cell culture at all times during the eHSC expansion. In certain embodiment, SB431542 is added to the medium in which eHSC (e.g., the Enriched eHSC) are cultured so as to be present at a concentration in the range of about 0.5 µM and 20 µM, 1 µM and 20 µM, 1 µM and 15 µM, 1 µM and 10 µM, 1.5 µM and 15 µM, 1.5 µM and 10 µM, 2 µM and 15 µM, 2 µM and 10 µM, 3 µM and 15 µM, 3 µM and 10 µM, 5 µM and 15 µM, 5 µM and 10 µM, 7.5 µM and 12.5 µM, or 8 µM and 12 µM. In certain embodiments, SB431542 is added to the culture medium so as to be present at a concentration of 0.5 µM, 1 µM, 2 µM, 3 µM, 4 µM, 5 µM, 6 µM, 7 µM, 8 µM, 9 µM, 10 µM, 11 µM, 12 µM, 13 µM, 14 µM or 15 µM. In some embodiments, SB431542 is added to the culture medium so as to be present at a concentration of no more than 20 µM. In some embodiments, an inhibitor of the TGFβ pathway (such as SB431542) is formulated in DMSO or another suitable carrier (e.g., can be contained as 10 mM solution in DMSO) for use in the expansion technique provided herein.

In specific embodiments, eHSC (e.g., the Enriched eHSC) are expanded in a basal medium, which can be supplemented with one or more growth factors described herein. A basal medium can comprise amino acids, carbon sources, vitamins, serum proteins (e.g. albumin), inorganic salts, divalent cations, buffers or any other element suitable for use in expansion of eHSC. Examples of such basal medium appropriate include, without limitation, StemSpan® SFEM—Serum-Free Expansion Medium (StemCell Technologies, Vancouver, Canada), StemSpan® H3000—Defined Medium (StemCell Technologies, Vancouver, Canada), CellGro® SCGM (CellGenix, Freiburg Germany), and StemPro®-34 SFM (Invitrogen). In some embodiments, eHSC (e.g., the Enriched eHSC) are expanded in serum-free medium. In other embodiments, eHSC (e.g., the Enriched eHSC) are expanded in medium containing fetal bovine serum (FBS), such as 5-30%, e.g., 20% of FBS. In a particular embodiment, eHSC (e.g., the Enriched eHSC) are expanded in Iscove's Modified Dulbeco's Media (IMDM) (Gibco) containing 20% FBS.

In particular embodiments, eHSC (e.g., the Enriched eHSC) are expanded in the presence of a Notch agonist, one or more growth factors, in the absence of an inhibitor of the TGFβ pathway (SB431542), in a serum-free medium.

In another particular embodiment, eHSC (e.g., the Enriched eHSC) are expanded in the presence of a Notch agonist, one or more growth factors, and an inhibitor of the TGFβ pathway (SB431542), in a medium comprising FBS (e.g., 5-30%, such as 20%, FBS).

In some embodiments of the invention, after expansion of the eHSC, eHSC are enriched in c-kit+ cells, Sca-1+ cells (mouse), CD34+ cells, CD49f+ cells, and/or CD34+CD90+ cells. In addition, the total number of c-kit+ cells, Sca-1+ cells, CD34+ cells, CD49f+ cells, and/or CD34+CD90+ cells can be determined by multi-parameter flow cytometry, as well as the percentage of such cells in the sample. Prior to cryopreservation or after thawing, an aliquot of the Expanded eHSC sample can be taken for determination of total nucleated cells and percentage of viable c-kit+ cells, viable Sca-1+ cells, viable CD34+ cells, viable CD49f+ cells, and/or viable CD34+CD90+ cells in order to calculate the total viable c-kit+ cells, Sca-1+ cells, CD34+, CD49f+ cells, and/or CD34+CD90+ cell number in the Expanded eHSC sample. In some embodiments, the Expanded eHSC contain more than 40%, more than 50%, more than 60%, more than 70%, or more than 80, or in the range of 50% to 100% or 60% to 90% of c-kit+ cells, Sca-1+ cells (mouse), CD34+ cells, CD49f+ cells, and/or CD34+CD90+ cells. In some embodiments, the Expanded eHSC are negative for or are depleted of Gr1 and/or F4/80. Presence or absence of Gr1 and F4/80 in the Expanded eHSC can also be determined by flow cytometry.

Numerous clinical studies have shown that the total nucleated cell dose and the CD34+ cell dose in stem cell grafts are highly correlated with neutrophil and platelet engraftment as well as the incidence of graft failure and early transplant-related complications (primarily lethal infections) following stem cell transplantation. Further, CD34+CD90+ cells have been shown to represent a sub-population of CD34+ cells capable of generating long-term engraftment. For example, at day 5-16 post culture initiation during expansion, a sample can be taken for determination of the total viable nucleated cell count.

In specific embodiments, total viable CD34+, CD34+ CD90+ cells (or other antigen-positive) cell numbers can be considered the potency assay for release of the final product for therapeutic use. Viability can be determined by any method known in the art, for example, by trypan blue exclusion or 7-AAD exclusion. Preferably, the total nucleated cell count (TNC) and other data are used to calculate the potency of the product. The percentage of viable CD34+ cells and/or viable CD34+CD90+ cells can be assessed by flow cytometry and use of a stain that is excluded by viable cells. The percentage of viable CD34+ cells=the number of CD34+ cells that exclude 7-AAD (or other appropriate stain) in an aliquot of the sample divided by the TNC (both viable and non-viable) of the aliquot. Viable CD34+ cells in the sample can be calculated as follows: Viable CD34+ cells=TNC of sample x % viable CD34+ cells in the sample. The proportional increase during enrichment or expansion in viable CD34+ cells can be calculated as follows: Total Viable CD34+ cells Post-culture/Total Viable CD34+ cells Pre-culture. As will be apparent, antigens other than or in addition to CD34 can be used.

The Expanded eHSC can contain both hematopoietic stem cells and hematopoietic progenitor cells.

The Expanded eHSC can be used without further purification or selection, or can be subject to further purification or selection. Once the Expanded eHSC are obtained, the Expanded eHSC may then be washed to remove the inhibitor of the TGFβ pathway such as SB431542 (and, optionally, one or more other agents used during the expansion procedure). In particular, the Expanded eHSC can be washed with PBS/2% FBS prior to administration to the patient. Upon washing, the Expanded eHSC can be resuspended in an appropriate cell suspension medium for short term use or in a long-term storage medium, for example, a medium suitable for cryopreservation.

In certain embodiments, the Expanded eHSC are differentiated into specific types of blood cells (e.g., red blood cells, platelets, neutrophils, megakaryocytes, etc.) ex vivo before administration to a patient. The Expanded eHSC can be differentiated into specific types of blood cells using any methods described herein or known in the art. For example, any of the growth factors known to promote cell differentiation into specific type of hematopoietic cells described herein or known in the art can be used. In particular, the following references describe methods for differentiation of eHSC that can be used for differentiation of the Expanded eHSC: Zeuner et al., 2012, Stem Cells 30:1587-96; Ebihara et al., 2012, Int J Hematol 95:610-6; Takayama & Eto, 2012, Cell Mol Life Sci 69:3419-28; Takayama & Eto, 2012, Methods Mol Biol 788:205-17; and Kimbrel & Lu, 2011, Stem Cells Int., March 8; doi:10.4061/2011/273076. In one embodiment, the Expanded eHSC are differentiated into red blood cells; such red blood cells can be administered to a patient. In one embodiment, the Expanded eHSC are differentiated into neutrophils; and such neutrophils can be administered to a patient. In one embodiment, the Expanded eHSC are differentiated into platelets; and such platelets can be administered to a patient. In certain embodiments, eHSC derived from cells obtained from a patient are expanded in accordance with the methods described herein (optionally, gene-corrected), differentiated into specific types of hematopoietic cells (e.g., red blood cells, neutrophils or platelets), and the differentiated cells produced from the Expanded eHSC are administered to the patient. In certain embodiments, eHSC derived from cells obtained from a patient are expanded in accordance with the methods described herein (optionally, gene-corrected), differentiated into specific types of hematopoietic cells (e.g., red blood cells, neutrophils or platelets), and the differentiated cells produced from the Expanded eHSC are stored (e.g., cryopreserved) for later administration to the patient.

As will be apparent, methods and products as described herein with respect to the Expanded eHSC will also apply to the differentiated cells produced from the Expanded eHSC, unless the context would indicate otherwise to one skilled in the art.

In some embodiments, the Expanded eHSC are obtained from embryonic hematopoietic stem cells derived from a patient to whom the Expanded eHSC are to be administered. In such embodiments, the embryonic hematopoietic stem cells can be derived from ESC, iPSC or reprogrammed non-pluripotent cells derived from the patient to whom the Expanded eHSC are to be administered. In a specific embodiment, adult cells can be obtained from a patient, such cells can be reprogrammed to iPSC and then eHSC, and then the eHSC are expanded in accordance with the methods described herein. In another specific embodiment, adult cells can be obtained from a patient, such non-pluripotent cells can be directly reprogrammed to eHSC, and then the eHSC are expanded in accordance with the methods described herein.

In specific embodiments, eHSC (e.g., Enriched eHSC) are derived from cells of a patient with a genetic disorder associated with a gene having a sequence defect, and such eHSC are genetically engineered to correct the sequence defect before administration to the patient (before or after expansion of the eHSC in accordance with the methods described herein). In one embodiment, eHSC (e.g., Enriched eHSC) are derived from cells of a patient with a genetic disorder associated with a gene having a sequence defect, and such eHSC are genetically engineered to correct the sequence defect prior to expansion, expanded in accordance with the methods described herein, and the genetically engineered and Expanded eHSC are administered to the patient. In an alternative embodiment, differentiated cells are produced from the genetically engineered Expanded eHSC, and such differentiated cells can be administered to the patient.

Cryopreservation and Thawing
Cryopreservation

Once the isolated eHSC, the Enriched eHSC, the Expanded eHSC, or cells differentiated therefrom are obtained, such isolated eHSC, Enriched eHSC, Expanded eHSC, or cells differentiated therefrom can be cryopreserved in accordance with the methods described below or known in the art.

In one embodiment, an Expanded eHSC population can be divided and frozen in one or more bags (or units). In another embodiment, two or more Expanded eHSC populations can be pooled, divided into separate aliquots, and each aliquot is frozen. In a preferred embodiment, a maximum of approximately 4 billion nucleated cells is frozen in a single bag. In a preferred embodiment, the Expanded eHSC are fresh, i.e., they have not been previously frozen prior to expansion or cryopreservation. The terms "frozen/freezing" and "cryopreserved/cryopreserving" are used interchangeably in the present application. Cryopreservation can be by any method in known in the art that freezes cells in viable form. The freezing of cells is ordinarily destructive. On cooling, water within the cell freezes. Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroys the cell. For a discussion, see Mazur, P., 1977, Cryobiology 14:251-272.

These injurious effects can be circumvented by (a) use of a cryoprotective agent, (b) control of the freezing rate, and (c) storage at a temperature sufficiently low to minimize degradative reactions.

Cryoprotective agents which can be used include but are not limited to dimethyl sulfoxide (DMSO) (Lovelock and Bishop, 1959, Nature 183:1394-1395; Ashwood-Smith, 1961, Nature 190:1204-1205), glycerol, polyvinylpyrrolidine (Rinfret, 1960, Ann. N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), and inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery ed., Butterworth, London, p. 59). In a preferred embodiment, DMSO is used, a liquid which is nontoxic to cells in low concentration. Being a small molecule, DMSO freely permeates the cell and protects intracellular organelles by combining with water to modify its freezability and prevent damage from ice formation. Addition of plasma (e.g., to a concentration of 20-25%) can augment the protective effect of DMSO. After addition of DMSO, cells should be kept at 0° C. until freezing, since DMSO concentrations of about 1% are toxic at temperatures above 4° C.

A controlled slow cooling rate can be critical. Different cryoprotective agents (Rapatz et al., 1968, Cryobiology 5(1):18-25) and different cell types have different optimal cooling rates (see e.g., Rowe and Rinfret, 1962, Blood 20:636; Rowe, 1966, Cryobiology 3(1):12-18; Lewis, et al., 1967, Transfusion 7(1):17-32; and Mazur, 1970, Science 168:939-949 for effects of cooling velocity on survival of marrow-stem cells and on their transplantation potential). The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve. For example, for marrow cells in 10% DMSO and 20% plasma, the optimal rate is 1° to 3° C./minute from 0° C. to −80° C. In a preferred embodiment, this cooling rate can be used for CB cells. The container holding the cells must be stable at cryogenic temperatures and allow for rapid heat transfer for effective control of both freezing and thawing. Sealed plastic vials (e.g., Nunc, Wheaton cryules) or glass ampules can be used for multiple small amounts (1-2 ml), while larger volumes (100-200 ml) can be frozen in polyolefin bags (e.g., Delmed) held between metal plates for better heat transfer during cooling. Bags of bone marrow cells have been successfully frozen by placing them in −80° C. freezers which, fortuitously, gives a cooling rate of approximately 3° C./minute).

In an alternative embodiment, the methanol bath method of cooling can be used. The methanol bath method is well-suited to routine cryopreservation of multiple small items on a large scale. The method does not require manual control of the freezing rate nor a recorder to monitor the rate. In a preferred embodiment, DMSO-treated cells are pre-cooled on ice and transferred to a tray containing chilled methanol which is placed, in turn, in a mechanical refrigerator (e.g., Harris or Revco) at −80° C. Thermocouple measurements of the methanol bath and the samples indicate the desired cooling rate of 1° to 3° C./minute. After at least two hours, the specimens have reached a temperature of −80° C. and can be placed directly into liquid nitrogen (−196° C.) for permanent storage.

After thorough freezing, the Expanded eHSC can be rapidly transferred to a long-term cryogenic storage vessel. In a preferred embodiment, samples can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Suitable racking systems are commercially available and can be used for cataloguing, storage, and retrieval of individual specimens.

Considerations and procedures for the manipulation, cryopreservation, and long-term storage of the hematopoietic stem cells, particularly from bone marrow or peripheral blood (e.g., mobilized peripheral blood), which are also largely applicable to the Expanded eHSC can be found, for example, in the following references, incorporated by reference herein: Gorin, 1986, Clinics In Haematology 15(1): 19-48; Bone-Marrow Conservation, Culture and Transplantation, Proceedings of a Panel, Moscow, Jul. 22-26, 1968, International Atomic Energy Agency, Vienna, pp. 107-186.

Other methods of cryopreservation of viable cells, or modifications thereof, are available and envisioned for use (e.g., cold metal-mirror techniques; Livesey and Linner, 1987, Nature 327:255; Linner et al., 1986, J. Histochem. Cytochem. 34(9):1123-1135; see also U.S. Pat. No. 4,199,022 by Senkan et al., U.S. Pat. No. 3,753,357 by Schwartz, U.S. Pat. No. 4,559,298 by Fahy).

In other embodiments, isolated eHSC, the Enriched eHSC or the Expanded eHSC are preserved by freeze-drying (see Simione, 1992, J. Parenter. Sci. Technol. 46(6):226-32).

Thawing

Following cryopreservation, frozen isolated eHSC, frozen Enriched eHSC or frozen Expanded eHSC can be thawed in accordance with the methods described below or known in the art.

Frozen cells are preferably thawed quickly (e.g., in a water bath maintained at 37°-41° C.) and chilled immediately upon thawing. In a specific embodiment, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

In an embodiment of the invention, the Expanded eHSC sample as thawed, or a portion thereof, can be infused for providing hematopoietic function in a human patient in need thereof. Several procedures, relating to processing of the thawed cells are available, and can be employed if deemed desirable.

It may be desirable to treat the cells in order to prevent cellular clumping upon thawing. To prevent clumping, various procedures can be used, including but not limited to, the addition before and/or after freezing of DNase (Spitzer et al., 1980, Cancer 45:3075-3085), low molecular weight dextran and citrate, hydroxyethyl starch (Stiff et al., 1983, Cryobiology 20:17-24), etc.

The cryoprotective agent, if toxic in humans, should be removed prior to therapeutic use of the thawed Expanded eHSC. In an embodiment employing DMSO as the cryopreservative, it is preferable to omit this step in order to avoid cell loss, since DMSO has no serious toxicity. However, where removal of the cryoprotective agent is desired, the removal is preferably accomplished upon thawing.

One way in which to remove the cryoprotective agent is by dilution to an insignificant concentration. This can be accomplished by addition of medium, followed by, if necessary, one or more cycles of centrifugation to pellet cells, removal of the supernatant, and resuspension of the cells. For example, intracellular DMSO in the thawed cells can be reduced to a level (less than 1%) that will not adversely affect the recovered cells. This is preferably done slowly to minimize potentially damaging osmotic gradients that occur during DMSO removal.

After removal of the cryoprotective agent, cell count (e.g., by use of a hemocytometer) and viability testing (e.g., by trypan blue exclusion; Kuchler, 1977, Biochemical Methods in Cell Culture and Virology, Dowden, Hutchinson & Ross, Stroudsburg, Pa., pp. 18-19; 1964, Methods in Medical Research, Eisen et al., eds., Vol. 10, Year Book Medical Publishers, Inc., Chicago, pp. 39-47) can be done to confirm cell survival. The percentage of viable antigen (e.g., CD34) positive cells in a sample can be determined by calculating the number of antigen positive cells that exclude 7-AAD (or other suitable dye excluded by viable cells) in an aliquot of the sample, divided by the total number of nucleated cells (TNC) (both viable and non-viable) in the aliquot of the sample. The number of viable antigen positive cells in the sample can be then determined by multiplying the percentage of viable antigen positive cells by TNC of the sample.

Optionally, the Expanded eHSC sample can undergo HLA typing either prior to cryopreservation and/or after cryopreservation and thawing. HLA typing can be performed using serological methods with antibodies specific for identified HLA antigens, or using DNA-based methods for detecting polymophisms in the HLA antigen-encoding genes for typing HLA alleles. In a specific embodiment, HLA typing can be performed at intermediate resolution using a sequence specific oligonucleotide probe method for HLA-A and HLA-B or at high resolution using a sequence based typing method (allele typing) for HLA-DRB1.

Genetically Engineered eHSC

In certain embodiments, the Expanded eHSC administered to the patient are non-recombinant.

In other embodiments, the isolated eHSC, the Enriched eHSC prior to expansion or the Expanded eHSC can be genetically engineered to correct a genetic defect in a subject. In certain embodiments, the isolated eHSC, the Enriched eHSC prior to expansion or the Expanded eHSC can be genetically engineered to correct a defective genetic sequence responsible for a genetic disorder in a patient using any gene editing techniques known in the art or described herein. For example, genes in the isolated eHSC, the Enriched eHSC prior to expansion or the Expanded eHSC can be corrected using nucleases, TALENs or adeno-associated virus vectors for generating genetically modified pigs (see Perez-Pinera et al., 2012, Curr Opin Chem Biol 16:268-77; Hafez & Hausner, 2012, Genome 55:553-69; Bedell et al., 2012, Nature 491:114-8; Durai et al., 2005, Nucleic Acids Res 33:5978-90; and Luo et al., 2012, J Genet Genomics 39:269-74). Using the techniques described in these references or other techniques known in the art the genome of the isolated eHSC, the Enriched eHSC prior to expansion or the Expanded eHSC can be modified in a targeted fashion, e.g., by directed mutagenesis/gene-editing of a specific DNA sequence of a gene, gene knockout or gene replacement.

In some embodiments, the isolated eHSC, the Enriched eHSC prior to expansion or the Expanded eHSC can be made to recombinantly express a gene product missing or defective in a subject, or recombinantly express an inhibitor of a gene product overexpressed or otherwise overactive or deleterious to a subject, prior to administration of such genetically engineered cells to the subject.

In another embodiment, the isolated eHSC, the Enriched eHSC prior to expansion or the Expanded eHSC can be genetically engineered to produce gene products that are beneficial upon transplantation of the genetically engineered cells to a subject. Such gene products include but are not limited to anti-inflammatory factors, e.g., anti-TNF, anti-IL-1, anti-IL-2, etc. In some embodiments, eHSC can be genetically engineered to "knock out" expression of MHC. The eHSC can be genetically engineered for use in gene therapy to adjust the level of gene activity in a subject to assist or improve the results of transplantation or to treat a disease caused by, for example, a deficiency in the recombinant gene. The eHSC are made recombinant by the introduction of a recombinant nucleic acid into the isolated eHSC, the Enriched eHSC or into the Expanded eHSC.

In its broadest sense, gene therapy refers to therapy performed by the administration of a nucleic acid to a subject. The nucleic acid, either directly or indirectly via its encoded protein, mediates a therapeutic effect in the subject. The present invention provides methods of gene therapy wherein a nucleic acid encoding a protein of therapeutic value (preferably to humans) is introduced into the eHSC, before or after expansion, such that the nucleic acid is expressible by the eHSC and/or their progeny, followed by administration of the recombinant Expanded eHSC to a subject. In other, preferred, embodiments, the present invention provides methods of gene therapy wherein a gene is corrected in the eHSC, before or after expansion as described above (see Perez-Pinera et al., 2012, Curr Opin Chem Biol 16:268-77; Hafez & Hausner, 2012, Genome 55:553-69; Bedell et al., 2012, Nature 491:114-8; Durai et al., 2005, Nucleic Acids Res 33:5978-90; and Luo et al., 2012, J Genet Genomics 39:269-74), such that the gene is corrected in the eHSC and its progeny, followed by administration of the recombinant Expanded eHSC to a subject.

In specific embodiments, eHSC are derived from iPSC or reprogrammed non-pluripotent cells obtained from a subject with an inherited disorder, such eHSC are (i) genetically engineered to correct a gene having a sequence defect associated with the inherited disorder using any of the methodology described herein or known in the art, (ii) expanded in accordance with the methods described herein, wherein the eHSC can be expanded either before or after gene-correction, and (iii) the gene-corrected expanded eHSC are administered to the subject in order to treat the inherited disorder. In one embodiment, eHSC are derived from iPSC obtained from a subject with an inherited disorder, such eHSC are (i) genetically engineered to correct a gene having a sequence defect associated with the inherited disorder using any of the methodology described herein or known in the art, (ii) expanded in accordance with the methods described herein, wherein the eHSC can be expanded either before or after gene-correction, and (iii) the gene-corrected expanded eHSC are administered to the subject in order to treat the inherited disorder. In some embodiments, the inherited disorder treated as described above is a hematopoietic disorder. In other embodiments, the inherited disorder treated as described above is a non-hematopoietic disorder, wherein the administration of the gene-corrected expanded eHSC results in delivery of eHSC to an organ or organs affected by such disorder (and, wherein, the gene-corrected expanded eHSC can be effective to treat such disorder).

The recombinant eHSC of the present invention can be used in any of the methods for gene therapy available in the art. Thus, the nucleic acid introduced into the cells may encode any desired protein, e.g., a protein missing or dysfunctional in a disease or disorder. The descriptions below are meant to be illustrative of such methods. It will be readily understood by those of skill in the art that the methods illustrated represent only a sample of all available methods of gene therapy.

For general reviews of the methods of gene therapy, see Gardlik et al., 2005, Med. Sci. Monit. 11:RA110-121; Lundstrom, 1999, J. Recept. Signal Transduct. Res. 19:673-686; Robbins and Ghivizzani, 1998, Pharmacol. Ther. 80:35-47; Pelegrin et al., 1998, Hum. Gene Ther. 9:2165-2175; Harvey and Caskey, 1998, Curr. Opin. Chem. Biol. 2:512-518; Guntaka and Swamynathan, 1998, Indian J. Exp. Biol. 36:539-535; Desnick and Schuchman, 1998, Acta Paediatr. Jpn. 40:191-203; Vos, 1998, Curr. Opin. Genet. Dev. 8:351-359; Tarahovsky and Ivanitsky, 1998, Biochemistry (Mosc) 63:607-618; Morishita et al., 1998, Circ. Res. 2:1023-1028; Vile et al., 1998, Mol. Med. Today 4:84-92; Branch and Klotman, 1998, Exp. Nephrol. 6:78-83; Ascenzioni et al., 1997, Cancer Lett. 118:135-142; Chan and Glazer, 1997, J. Mol. Med. 75:267-282. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In an embodiment in which recombinant eHSC are used in gene therapy, a gene whose expression is desired in a subject is introduced into the eHSC such that it is expressible by the cells and/or their progeny, and the recombinant cells are then administered in vivo for therapeutic effect.

Recombinant Expanded eHSC can be used in any appropriate method of gene therapy, as would be recognized by those in the art upon considering this disclosure. The resulting action of recombinant cell populations administered to a subject can, for example, lead to the activation or inhibition of a pre-selected gene in the subject, thus leading to improvement of the diseased condition afflicting the subject.

In this embodiment, the desired gene is introduced into the eHSC or its progeny prior to administration in vivo of the resulting recombinant cell. Such introduction can be carried out by any method known in the art, including but not limited to transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the gene to the cell, so that the gene is expressible by the cell and preferably heritable and expressible by its cell progeny. Usually, the method of transfer includes the transfer of a selectable marker to the cells. The cells are then placed under selection to isolate those cells that have taken up and are expressing the transferred gene. Those cells are then delivered to a subject.

Retroviral vectors (see Miller et al., 1993, Meth. Enzymol. 217:581-599), and specifically lentiviral, can be used in gene therapy. In such embodiments, the gene to be used in gene therapy is cloned into the retroviral vector for its delivery into eHSC. In particular embodiments, a retroviral vector for use in gene therapy contains all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions.

More detail about retroviral vectors can be found in Boesen et al., 1994, Biotherapy 6:291-302, Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are also of use in gene therapy. See Kozarsky and Wilson, 1993, Current Opinion in Genetics and Development 3:499-503, Rosenfeld et al., 1991, Science 252:431-434; Rosenfeld et al., 1992, Cell 68:143-155; and Mastrangeli et al., 1993, J. Clin. Invest. 91:225-234.

It has been proposed that adeno-associated virus (AAV) be used in gene therapy (Walsh et al., 1993, Proc. Soc. Exp. Biol. Med. 204:289-300). It has also been proposed that alphaviruses be used in gene therapy (Lundstrom, 1999, J. Recept. Signal Transduct. Res. 19:673-686).

Other methods of gene delivery in gene therapy include the use of mammalian artificial chromosomes (Vos, 1998, Curr. Op. Genet. Dev. 8:351-359); liposomes (Tarahovsky and Ivanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282).

A desired gene can be introduced intracellularly and incorporated within eHSC DNA for expression, by homologous recombination (Koller and Smithies, 1989, Proc. Natl. Acad. Sci. USA 86:8932-8935; Zijlstra et al., 1989, Nature 342:435-438).

In a specific embodiment, isolated eHSC or the Enriched eHSC or the Expanded eHSC are genetically engineered to express a gene that is deficient in the patient to whom such eHSC are to be administered. In another specific embodiment, isolated eHSC or the Enriched eHSC or the Expanded eHSC are genetically engineered to express an inhibitor of a gene that is overexpressed or overactive in the patient to whom such eHSC are to be administered.

In a specific embodiment, the desired gene recombinantly expressed in the eHSC or their progeny after expansion to be introduced for purposes of gene therapy comprises an inducible promoter operably linked to the coding region, such that expression of the recombinant gene is controllable by controlling the presence or absence of the appropriate inducer of transcription.

The methods described herein and/or known in the art to make genetically engineered eHSCs can alternatively be applied to genetically engineer cells from which such eHSC can be derived, such embryonic stem cells, induced pluripotent stem cells (iPSC), or non-pluripotent cells that are reprogrammed to produce eHSC. In some embodiments, ESC, iPSC or non-pluripotent cells that are reprogrammed to produce eHSC are genetically engineered to correct a genetic defect prior to obtaining eHSC from such cells.

Therapeutic Methods

The ideal therapeutic product for treatment of chemotherapy or radiation induced pancytopenia is one that, when infused, would give rise to rapid hematopoietic reconstitution, especially of granulocytes, and also facilitate autologous recovery of hematopoiesis.

The Expanded eHSC, whether recombinantly expressing a desired gene, having been corrected for a defective gene, or not, can be administered into a human patient in need thereof for hematopoietic function for the treatment of disease or injury or for gene therapy by any method known in the art which is appropriate for the Expanded eHSC and the transplant site. Preferably, the Expanded eHSC are transplanted (infused) intravenously. In one embodiment, the Expanded eHSC differentiate into cells of the myeloid lineage in the patient. In another embodiment, the Expanded eHSC differentiate into cells of the lymphoid lineage in the patient.

In one embodiment, the transplantation of the Expanded eHSC is autologous. In such embodiments, before expansion, cells are isolated from tissues of a subject to whom the Expanded eHSC are to be administered, reprogrammed to iPSC and then eHSC, or directly reprogrammed to eHSC and, optionally, gene-corrected as described above. In other embodiments, the transplantation of the Expanded eHSC is non-autologous. In some of these embodiments, the transplantation of the Expanded eHSC is allogeneic. For non-autologous transplantation, the recipient can be given an immunosuppressive drug to reduce the risk of rejection of the transplanted cells. In some embodiments, the transplantation of the Expanded eHSC is syngeneic.

In specific embodiments, eHSC are isolated from a subject for expansion prior to the subject's exposure to chemotherapy, and the Expanded eHSC obtained using the methods described herein from the isolated eHSC of the subject are administered to the subject following exposure to chemotherapy.

In specific embodiments, eHSC are isolated from a subject with a hematopoietic disorder, the isolated eHSC are expanded in accordance with the methods described herein, the isolated eHSC are also genetically engineered in order to improve or correct the hematopoietic disorder as described in Section 6.8 before or after the expansion, and such genetically-engineered and Expanded eHSC are administered to the subject.

In specific embodiments, the Expanded eHSC are not administered to the patient within 12 hours of administration of a myeloid progenitor cell population as defined in International Patent Publication Nos. WO 2006/047569 A2 and/or WO 2007/095594 A2. In other specific embodiments, the Expanded eHSC are not administered to the patient within 18 or 24 or 36 or 48 or 72 or 96 hours or within 7, 10, 14, 21, 30 days of administration of such a myeloid progenitor cell population to the patient.

In a preferred embodiment, the Expanded eHSC sample that is administered to the patient is derived from one individual.

In some embodiments, the Expanded eHSC sample that is administered to the patient has been cryopreserved and thawed prior to administration. In other embodiments, the Expanded eHSC sample that is administered to the patient is fresh, i.e., it has not been cryopreserved prior to administration.

In certain embodiments, the Expanded eHSC are intended to provide short-term engraftment. Short-term engraftment usually refers to engraftment that lasts for up to a few days to few weeks, preferably 4 weeks, post-transplantation of the Expanded eHSC. In some embodiments, the Expanded eHSC are effective to provide engraftment 1, 2, 3, 4, 5, 6, 7, 8, 9, 10 days; or 1, 2, 3, 4 weeks after administration of the Expanded eHSC to a patient (e.g., a human patient). In other embodiments, the Expanded eHSC are intended to provide long-term engraftment. Long-term engraftment usually refers to engraftment that is present months to years post-transplantation of the Expanded eHSC. In some embodiments, the Expanded eHSC are effective to provide engraftment when assayed at 8, 9, 10 weeks; 2, 3, 4, 5, 6, 7, 8, 9, 10, 11, 12 months (or more than 2, 3, 4, 5, 6, 7, 8, 9, 10, 11, 12 months); or 1, 2, 3, 4, 5 years (or more than 1, 2, 3, 4, 5 years) after administration of the Expanded eHSC to a patient. In some embodiments, the Expanded eHSC are intended to provide both short-term and long-term engraftment. In certain embodiments, the Expanded eHSC provide short-term and/or long-term engraftment in a patient, preferably, a human.

In some embodiments, the Expanded eHSC are effective to provide engraftment when assayed at 1, 2, 3, 4, 5, 6, 7, 8, 9, 10 days (or more than 1, 2, 3, 4, 5, 6, 7, 8, 9, 10 days); 1, 2, 3, 4, 5, 6, 7, 8, 9, 10 weeks (or more than 1, 2, 3, 4, 5, 6, 7, 8, 9, 10 weeks); 1; 2, 3, 4, 5, 6, 7, 8, 9, 10, 11, 12 months (or more than 1, 2, 3, 4, 5, 6, 7, 8, 9, 10, 11, 12 months); or 1, 2, 3, 4, 5 years (or more than 1, 2, 3, 4, 5 years) after administration of the Expanded eHSC to a patient (e.g., a human patient). In other embodiments, the Expanded eHSC are effective to provide engraftment when assayed within 1, 2, 3, 4, 5, 6, 7, 8, 9, 10 days (or less than 1, 2, 3, 4, 5, 6, 7, 8, 9, 10 days); 1, 2, 3, 4, 5, 6, 7, 8, 9, 10 weeks (or less than 1, 2, 3, 4, 5, 6, 7, 8, 9, 10 weeks); or 1; 2, 3, 4, 5, 6, 7, 8, 9, 10, 11, 12 months (or less than 1, 2, 3, 4, 5, 6, 7, 8, 9, 10, 11, 12 months) after administration of the Expanded eHSC to a patient (e.g., a human patient). In specific embodiments, the Expanded eHSC are effective to provide engraftment when assayed within 10 days, 2 weeks, 3 weeks, 4 weeks, 6 weeks, 6 weeks, or 13 weeks after administration of the Expanded eHSC to a patient (e.g., a human patient).

Suitable methods of administration of the Expanded eHSC are encompassed by the present invention. The Expanded eHSC populations can be administered by any convenient route, for example by infusion or bolus injection, and may be administered together with other biologically active agents. Administration can be systemic or local.

The titer of the Expanded eHSC administered which will be effective in the treatment of a particular disorder or condition will depend on the nature of the disorder or condition, and can be determined by standard clinical techniques. In addition, in vitro and in vivo assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. In specific embodiments, suitable dosages of the Expanded eHSC for administration are generally about at least $5 \times 10^6$, $10^7$, $5 \times 10^7$, $75 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ CD34+ cells per kilogram patient weight, and most preferably about $10^7$ to about $10^{12}$ CD34+ cells per kilogram patient weight, and can be administered to a patient once, twice, three or more times with intervals as often as needed. In a specific embodiment, a single Expanded eHSC sample provides one or more doses for a single patient. In one specific embodiment, a single Expanded eHSC sample provides four doses for a single patient.

In certain embodiments, the patient is a human patient, preferably a human patient with a hematopoietic disorder or an immunodeficient human patient.

In a specific embodiment, the Expanded eHSC population administered to a human patient in need thereof can be a pool of two or more samples derived from a single human.

Pharmaceutical Compositions

The invention provides methods of treatment by administration to a patient of a pharmaceutical (therapeutic) composition comprising a therapeutically effective amount of recombinant or non-recombinant Expanded eHSC produced by the methods of the present invention as described herein above.

The present invention provides pharmaceutical compositions. Such compositions comprise a therapeutically effective amount of the Expanded eHSC, and a pharmaceutically acceptable carrier or excipient. Such a carrier can be but is not limited to saline, buffered saline, dextrose, water, glycerol, ethanol, and combinations thereof. The carrier and composition preferably are sterile. Suitable pharmaceutical carriers are described in Remington: The Science and Practice of Pharmacy, 21st Edition, David B. Troy, ed., Lippicott Williams & Wilkins (2005), which is incorporated by reference herein in its entirety, and specifically for the material related to pharmaceutical carriers and compositions. The pharmaceutical compositions described herein can be formulated in any manner known in the art.

The formulation should suit the mode of administration. Expanded eHSC can be resuspended in a pharmaceutically acceptable medium suitable for administration to a mammalian host. In preferred embodiments, the pharmaceutical composition is acceptable for therapeutic use in humans. The composition, if desired, can also contain pH buffering agents.

The pharmaceutical compositions described herein can be administered via any route known to one skilled in the art to be effective. In a preferred embodiment, the composition is formulated in accordance with routine procedures as a pharmaceutical composition adapted for intravenous administration to a patient (e.g., a human). Typically, compositions for intravenous administration are solutions in sterile isotonic aqueous buffer. Where necessary, the composition may also include a solubilizing agent and a local anesthetic such as lidocaine to ease pain at the site of the injection.

In specific embodiments, the compositions described herein are formulated for administration to a patient with one or more additional therapeutic active ingredients.

Therapeutic Uses of the Expanded eHSC

The Expanded eHSC of the present invention can be used to provide hematopoietic function to a patient in need thereof, preferably a human patient. In other embodiments, the patient is a cow, a pig, a horse, a dog, a cat, or any other animal, preferably a mammal.

The patient to whom the Expanded eHSC are administered is a patient of any age post-birth, e.g., a newborn, an infant, a child or an adult (e.g., a human newborn, a human infant, a human child or a human adult).

In one embodiment, administration of Expanded eHSC of the invention is for the treatment of immunodeficiency. In a preferred embodiment, administration of Expanded eHSC of the invention is for the treatment of pancytopenia or for the treatment of neutropenia. The immunodeficiency in the patient, for example, pancytopenia or neutropenia, can be the result of an intensive chemotherapy regimen, myeloablative regimen for hematopoietic cell transplantation (HCT), or exposure to acute ionizing radiation. Exemplary chemotherapeutics that can cause prolonged pancytopenia or prolonged neutropenia include, but are not limited to alkylating agents such as cisplatin, carboplatin, and oxaliplatin, mechlorethamine, cyclophosphamide, chlorambucil, and ifosfamide. Other chemotherapeutic agents that can cause prolonged pancytopenia or prolonged neutropenia include azathioprine, mercaptopurine, vinca alkaloids, e.g., vincristine, vinblastine, vinorelbine, vindesine, and taxanes. In particular, a chemotherapy regimen that can cause prolonged pancytopenia or prolonged neutropenia is the administration of clofarabine and Ara-C.

In one embodiment, the patient is in an acquired or induced aplastic state.

The immunodeficiency in the patient also can be caused by exposure to acute ionizing radiation following a nuclear attack, e.g., detonation of a "dirty" bomb in a densely populated area, or by exposure to ionizing radiation due to radiation leakage at a nuclear power plant, or exposure to a source of ionizing radiation, raw uranium ore.

Transplantation of Expanded eHSC of the invention can be used in the treatment or prevention of hematopoietic disorders and diseases. In one embodiment, the Expanded eHSC are administered to a patient with a hematopoietic deficiency. In one embodiment, the Expanded eHSC are used to treat or prevent a hematopoietic disorder or disease characterized by a failure or dysfunction of normal blood cell production and cell maturation. In another embodiment, the Expanded eHSC are used to treat or prevent a hematopoietic disorder or disease resulting from a hematopoietic malignancy. In yet another embodiment, the Expanded eHSC are used to treat or prevent a hematopoietic disorder or disease resulting from immunosuppression, particularly immunosuppression in subjects with malignant, solid tumors. In yet another embodiment, the Expanded eHSC are used to treat or prevent an autoimmune disease affecting the hematopoietic system. In yet another embodiment, the Expanded eHSC are used to treat or prevent a genetic or congenital hematopoietic disorder or disease.

Examples of particular hematopoietic diseases and disorders which can be treated by the Expanded eHSC of the invention include but are not limited to those listed in Table 2, infra.

TABLE 2

DISEASES OR DISORDERS WHICH CAN BE TREATED BY ADMINISTERING EXPANDED eHSC OF THE INVENTION

Diseases Resulting from a Failure or Dysfunction
of Normal Blood Cell Production and Maturation
hyperproliferative stem cell disorders aplastic anemia
pancytopenia
agranulocytosis
thrombocytopenia
red cell aplasia
Blackfan-Diamond syndrome due to drugs, radiation, or infection
Idiopathic
II. Hematopoietic malignancies acute lymphoblastic (lymphocytic) leukemia
chronic lymphocytic leukemia
acute myelogenous leukemia
chronic myelogenous leukemia
acute malignant myelosclerosis
multiple myeloma
polycythemia vera
agnogenic myelometaplasia
Waldenstrom's macroglobulinemia
Hodgkin's lymphoma
non-Hodgkin's lymphoma
III. Immunosuppression in patients with malignant, solid tumors malignant melanoma
carcinoma of the stomach

TABLE 2-continued

DISEASES OR DISORDERS WHICH CAN BE TREATED BY
ADMINISTERING EXPANDED eHSC OF THE INVENTION ovarian carcinoma
breast carcinoma
small cell lung carcinoma
retinoblastoma
testicular carcinoma
glioblastoma
rhabdomyosarcoma
neuroblastoma
Ewing's sarcoma
lymphoma
IV Autoimmune diseases rheumatoid arthritis
diabetes type I
chronic hepatitis
multiple sclerosis
systemic lupus erythematosus
V. Genetic (congenital) disorders anemias
familial aplastic
Fanconi's syndrome (Fanconi anemia)
Bloom's syndrome
pure red cell aplasia (PRCA)
dyskeratosis congenital
Blackfan-Diamond syndrome
congenital dyserythropoietic syndromes I-IV
Chwachmann-Diamond syndrome
dihydrofolate reductase deficiencies
formamino transferase deficiency
Lesch-Nyhan syndrome
congenital spherocytosis
congenital elliptocytosis
congenital stomatocytosis
congenital Rh null disease
paroxysmal nocturnal hemoglobinuria
G6PD (glucose-6-phosphate dehydrogenase) variants 1, 2, 3
pyruvate kinase deficiency
congenital erythropoietin sensitivity deficiency
sickle cell disease and trait (Sickle cell anemia)
thalassemia alpha, beta, gamma
met-hemoglobinemia
congenital disorders of immunity
severe combined immunodeficiency disease (SCID)
bare lymphocyte syndrome
ionophore-responsive combined immunodeficiency
combined immunodeficiency with a capping abnormality
nucleoside phosphorylase deficiency
granulocyte actin deficiency
infantile agranulocytosis
Gaucher's disease
adenosine deaminase deficiency
Kostmann's syndrome
reticular dysgenesis
congenital leukocyte dysfunction syndromes
VI. Others osteopetrosis
myelosclerosis
acquired hemolytic anemias
acquired immunodeficiencies
infectious disorders causing primary or secondary
immunodeficiencies
bacterial infections (e.g., Brucellosis, Listerosis, tuberculosis, leprosy)
parasitic infections (e.g., malaria, Leishmaniasis)
fungal infections
disorders involving disproportions in lymphoid cell sets and impaired
immune functions due to aging
phagocyte disorders
Kostmann's agranulocytosis
chronic granulomatous disease
Chediak-Higachi syndrome
neutrophil actin deficiency
neutrophil membrane GP-180 deficiency
metabolic storage diseases
mucopolysaccharidoses
mucolipidoses

TABLE 2-continued

DISEASES OR DISORDERS WHICH CAN BE TREATED BY
ADMINISTERING EXPANDED eHSC OF THE INVENTION miscellaneous disorders involving immune mechanisms
Wiskott-Aldrich Syndrome
α1-antitrypsin deficiency In one embodiment, the Expanded eHSC are administered to a patient with a hematopoietic deficiency. Hematopoietic deficiencies whose treatment with the Expanded eHSC of the invention is encompassed by the methods of the invention include but are not limited to decreased levels of either myeloid, erythroid, lymphoid, or megakaryocyte cells of the hematopoietic system or combinations thereof, including those listed in Table 2. In one embodiment, the Expanded eHSC are administered prenatally to a fetus diagnosed with a hematopoietic deficiency.

Among conditions susceptible to treatment with the Expanded eHSC of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage.

Expanded eHSC also can be used in the treatment or prevention of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome, myelofibrosis, thrombocytopenia. Severe thrombocytopenia may result from genetic defects such as Fanconi's Anemia, Wiscott-Aldrich, or May-Hegglin syndromes and from chemotherapy and/or radiation therapy or cancer. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Thrombocytopenia may also result from marrow invasion by carcinoma, lymphoma, leukemia or fibrosis.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anticonvulsants such as phenytoin or carbamazepine, antithyroids such as propylthiouracil and methimazole and diuretics. Transplantation of the Expanded eHSC can be used in preventing or treating the bone marrow suppression or hematopoietic deficiencies which often occur in subjects treated with these drugs.

Hematopoietic deficiencies may also occur as a result of viral, microbial or parasitic infections and as a result of treatment for renal disease or renal failure, e.g., dialysis. Transplantation of the Expanded eHSC populations may be useful in treating such hematopoietic deficiency.

Various immunodeficiencies, e.g., in T and/or B lymphocytes, or immune disorders, e.g., rheumatoid arthritis, may also be beneficially affected by treatment with the Expanded eHSC. Immunodeficiencies may be the result of viral infections (including but not limited to HIVI, HIVII, HTLVI, HTLVII, HTLVIII), severe exposure to radiation, cancer therapy or the result of other medical treatment.

In specific embodiments, the Expanded eHSC are used for the treatment of multiple myeloma, non-Hodgkin's lymphoma, Hodgkin's disease, neuroblastoma, germ cell tumors, autoimmune disorder (e.g., Systemic lupus erythematosus (SLE) or systemic sclerosis), amyloidosis, acute myeloid leukemia, acute lymphoblastic leukemia, chronic myeloid leukemia, chronic lymphocytic leukemia, myeloproliferative disorder, myelodysplastic syndrome, aplastic anemia, pure red cell aplasia, paroxysmal nocturnal hemoglobinuria, Fanconi anemia, Thalassemia major, Sickle cell anemia, Severe combined immunodeficiency (SCID), Wiskott-Aldrich syndrome, Hemophagocytic lymphohistiocytosis (HLH), or inborn errors of metabolism (e.g., mucopolysaccharidosis, Gaucher disease, metachromatic leukodystrophies or adrenoleukodystrophies). In some embodiments, the Expanded eHSC are used for the treatment of an inherited immunodeficient disease, an autoimmune disease and/or a hematopoietic disorder.

In one embodiment, the Expanded eHSC are for replenishment of hematopoietic cells in a patient who has undergone chemotherapy or radiation treatment. In a specific embodiment, the Expanded eHSC are administered to a patient that has undergone chemotherapy or radiation treatment. In a specific embodiment, the Expanded eHSC are administered to a patient who has HIV (e.g., for replenishment of hematopietic cells in a patient who has HIV).

In certain embodiments, the Expanded eHSC are administered into the appropriate region of a patient's body, for example, by injection into the patient's bone marrow.

In some embodiments, the patient to whom the Expanded eHSC are administered is a bone marrow donor, at risk of depleted bone marrow, or at risk for depleted or limited blood cell levels. In one embodiment, the patient to whom the Expanded eHSC is administered is a bone marrow donor prior to harvesting of the bone marrow. In one embodiment, the patient to whom the Expanded eHSC is administered is a bone marrow donor after harvesting of the bone marrow. In one embodiment, the patient to whom the Expanded eHSC is administered is a recipient of a bone marrow transplant. In one embodiment, the patient to whom the Expanded eHSC is administered is elderly, has been exposed or is to be exposed to an immune depleting or myeloablative treatment (e.g., chemotherapy, radiation), has a decreased blood cell level, or is at risk of developing a decreased blood cell level as compared to a control blood cell level. In one embodiment, the patient has anemia or is at risk for developing anemia. In one embodiment, the patient has blood loss due to, e.g., trauma, or is at risk for blood loss. The Expanded eHSC can be administered to a patient, e.g., before, at the same time, or after chemotherapy, radiation therapy or a bone marrow transplant. In specific embodiments, the patient has depleted bone marrow related to, e.g., congenital, genetic or acquired syndrome characterized by bone marrow loss or depleted bone marrow. In one embodiment, the patient is in need of hematopoiesis. In one embodiment, eHSC are derived from a patient (e.g., from iPSC or reprogrammed non-pluripotent cells of the patient) that will undergo an immune depleting procedure (e.g., chemotherapy, radiation, or bone marrow extraction from donor), the eHSC are expanded as described herein, and after the treatment the Expanded eHSC are administered to the patient. In one embodiment, eHSC are derived from a patient (e.g., from iPSC or reprogrammed non-pluripotent cells of the patient) that has a hematopoietic disorder, the eHSC are expanded as described herein and genetically engineered to correct or improve the hematopoietic disorder, and the genetically engineered and Expanded eHSC are administered to the patient.

Kits

The invention also provides a pharmaceutical pack or kit comprising one or more containers. In a preferred embodiment, a kit of the invention comprises, in one or more containers, a Notch agonist (such as purified Notch agonist) and an inhibitor of the TGFβ pathway. In a specific embodiment, the Notch agonist is Delta1Ext-IgG, and the inhibitor of the TGFβ pathway is SB431542. In one embodiment, a Notch agonist and an inhibitor of the TGFβ pathway are stored in two separate containers of the kit. In certain embodiments, each of the ingredients of the kit listed herein is provided in a separate container. In other embodiments, two or more of the ingredients of the kit listed herein are provided in a same container.

The kit may additionally comprise one or more purified growth factors, for example, one or more growth factors that promote proliferation but not differentiation of eHSC. Such one or more growth factors may be stored in a container separate from the container comprising a Notch agonist and/or in a container separate from the container comprising an inhibitor of the TGFβ pathway. In some embodiments, the kit may further comprise, in a separate container, one or more purified growth factors that promote the differentiation of eHSC. In a specific embodiment, the one or more purified growth factors are SCF, Flt-3L and IL-3.

In certain embodiments, cell culture medium is also provided in the kit. In other embodiments, the solid phase on which Delta1Ext-IgG can be coated is also provided in the kit (for example, such a kit may contain one or more tissue culture dishes coated with Delta1Ext-IgG). In certain embodiments, the kit also comprises fibronectin (e.g., an immobilized fibronectin) or a fragment thereof (e.g., CH-296). In certain embodiments, fibronectin or a fragment thereof are provided in a separate container. In some embodiments, fibronectin or a fragment thereof is provided in the same container as a Notch agonist. In a particular embodiment, fibronectin or a fragment thereof is provided in the same container as a Notch agonist, wherein both fibronectin or a fragment thereof and the Notch agonist are coated on a solid phase.

The kit may further comprise one or more containers filled with isolated eHSC or the Enriched eHSC. The Notch agonist and the one or more growth factors provided in the described kit (and, optionally, the inhibitor of the TGFβ pathway) are together effective to expand the Enriched eHSC exposed to these ingredients of the kit in culture. In certain embodiment, a kit comprises one or more containers filled with the Enriched eHSC or with the Expanded eHSC produced by the methods of the invention and/or reagents to prepare said cells, or with reagents for the genetic manipulation of the cells.

The kit may additionally comprise a solution or a buffer (in a separate container, or in the same container as inhibitor of the TGFβ pathway and/or the Notch agonist).

In some embodiments, the kit comprises a container with one or more antibodies (e.g., anti-CD34, anti-CD45, anti-VE-Cadherin, anti-CD41, anti-c-kit antibodies, or any other antibodies to markers/antigens described herein or known in the art).

Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLE

The data presented herein show that embryonic hematopoietic stem cells (eHSC) can be expanded using a combination of a Notch agonist, one or more growth factors, and, optionally, an inhibitor of the TGFβ pathway. In particular, the data presented herein show that eHSC from an embryonic source, in particular, from the aorta-gonad-mesonephros region of an embryo, can be expanded using a combination of an immobilized Notch ligand, Delta1ext-IgG, hematopoietic cytokines, and a small molecule inhibitor of the TGFβ pathway (SB431542). Further, the data demonstrate that culturing of eHSC in the presence of a combination of immobilized Notch ligand, Delta1ext-IgG, hematopoietic cytokines, and a small molecule inhibitor of the TGFβ pathway (SB431542) promotes expansion of progenitors with erythromyeloid colony forming potential and T/B-lymphoid potential in vitro, with concurrent maturation of surface phenotype resembling fetal liver-stage HSC. Furthermore, the data presented herein suggest that expansion of eHSC using a combination of a Notch agonist, cytokines, and, optionally, a small molecule inhibitor of the TGFβ pathway, leads to generation of cells with rapidly engrafting myeloid and lymphoid capacity when transplanted into a patient. In addition, the results presented herein establish the optimal concentration of Delta1ext-IgG to be used for expansion of eHSC in order to achieve long-term, multilineage hematopoietic reconstitution in a patient. In particular, the inventors found that long-term, multilineage hematopoietic reconstitution capacity of expanded cells transplanted into irradiated adult mice appears to be optimal when Delta1ext-IgG is used at the concentration of about 2.5 µg/ml.

Materials and Methods

Mice:

Wild type C57Bl6/J7 (Ly5.2) and Ly6a-eGFP mice (B6.Cg-Tg(Ly6a-EGFP)G5Dzk/J), hemizygous for the Ly6a-GFP transgene, were from Jackson Laboratories. Congenic C57BL/6.SJL-Ly5.1-Pep3b (Ly5.1) mice were bred at the Fred Hutchinson Cancer Research Center. C57Bl6/J7 Ly5.2 male and female mice or Ly6a-eGFP hemizygous males crossed to wild type C57Bl6/J7 female were used for timed matings and the morning that plug was detected was considered 0.5 days post coitum (dpc). All animal studies were conducted in accordance with the NIH guidelines for humane treatment of animals and were approved by the Institutional Animal Care and Use Committee.

Embryo Dissections and Cell Sorting:

Embryos were harvested from pregnant females at 9.5 to 11.5 dpc, dissected free of maternal tissue and washed extensively in PBS containing 10% fetal bovine serum (FBS). Embryo age was precisely time by counting somite numbers. Yolks sac was dissected free from the embryo. For AGM dissections, 30 gauge needles were used to remove the caudal and rostral portions of the embryo above the forelimbs and below the hindlimbs, and subsequently dissect off the dorsal somite tissue and ventral abdominal contents. The embryo was then splayed open lying on its dorsal surface and remaining tissues surrounding the urogenital ridges were further dissected, leaving the intact AGM containing the dorsal aorta centrally. For embryos prior to AGM stage (E9.5 or less), the P-Sp region was dissected by removing the rostral and caudal portions of the embryo. Dissected yolk sac or AGM/P-Sp tissues were pooled and treated with 0.25% collagenase (Stem Cell Technologies, Vancouver, Canada) for 25-30 minutes at 37° C., pipetted to single cell suspension, and washed with PBS containing 10% FBS. For Ly6a-eGFP transgenic embryos, dissected embryos were processed separately and pooled for sorting, if indicated, following confirmation of GFP expression. Cells were incubated with anti-mouse CD16/CD32 (FcγRII block) and stained with the following monoclonal antibodies: APC-conjugated CD45 (clone 30-F11) or APC-conjugated CD41 (clone MWReg30, eBioscience) and unconjugated VE-Cadherin/CD144 (clone 11D4.1), or corresponding isotype controls. Following incubation with primary antibodies, cells were washed twice with PBS/FBS and secondary staining was performed with PE-conjugated mouse anti Rat IgG2a (clone RG7/1.30). All antibodies were from BD Biosciences unless otherwise indicated. DAPI staining was used to gate out dead cells. All reagents for cell staining were diluted in PBS/FBS and staining was carried out on ice or at 4° C. Cells were sorted on a Vantage Aria.

Cell Culture:

Jagged1ext-IgG and Delta1ext-IgG were generated as previously described (Varnum-Finney B, Wu L, Yu M, et al. J Cell Sci. 2000; 113 Pt 23:4313-4318). Non-tissue culture treated plates (Falcon, B D) were incubated with Delta1ext-IgG at (dose range from 0.3 µg/ml to 5 µg/ml), Jagged1ext-IgG at 20 µg/ml (a dose previously demonstrated to achieve a concentration equivalent to Delta1ext-IgG by ELISA), or human IgG1 (Sigma-Aldrich) diluted in PBS together with 5 µg/ml RetroNectin (r-fibronectin CH-296, Takara Bio), incubated overnight at 4° C. Wells were washed extensively with PBS prior to adding media. Media consisted of either Iscove's Modified Dulbeco's Media (IMDM) (Gibco) containing 20% fetal bovine serum (FBS) (Hyclone), Penicillin/Streptomycin (Sigma), small molecule inhibitor of TGFβ pathway (10 µM SB431541, added 1:1000 from stock 10 mM solution in DMSO, Tocris Biochemicals), and hematopoietic cytokines: recombinant murine Stem Cell Factor (SCF), recombinant human FLT3 ligand (FLT3L), recombinant human interleukin-6 (IL-6), and recombinant interleukin-3 (IL-3), each at 100 ng/ml, recombinant human thrombopoietin (TPO) at 20 ng/ml, and recombinant human interleukin-11 (IL-11) at 10 ng/ml. Freshly sorted cells from dissected embryos were re-suspended in media with cytokines and added to coated wells. Cells were passaged to larger wells prepared as above once cells were nearly confluent, when necessary. For most experiments, cells were harvested for phenotypic analysis, CFU or transplantation assays at day 5 of culture, unless otherwise indicated.

Limit Dilution Analysis:

Freshly sorted AGM cells were cultured in two-fold serial dilutions in 5 replicate samples per dilution on 96 wells incubated with Delta1ext-IgG containing media with cytokines as described above. Following seven days in culture, wells containing colonies of expanded cells were enumerated and individual wells harvested for cell surface analysis by staining with antibodies to c-kit and sca-1 as described below. Wells containing colonies of cells that stained for both c-kit and sca-1 were considered positive and L-Calc software (Stem Cell Technologies) was used to determine frequency of cells generating Sca-1+/c-kit+ colonies.

Cell Surface Analysis:

Cells were harvested from freshly isolated P-Sp/AGM or yolk sac as described above or gently pipetted from tissue cultures wells and washed with PBS with 2% FBS. Cells were pre-incubated with anti-mouse CD16/CD32 (FcγRII block) and then stained with various combinations of the following monoclonal antibodies for cell surface analysis: APC-conjugated CD45 (clone 30-F11), APC-conjugated CD41 (clone MWReg30, eBioscience), purified VE-Cadherin/CD144 (clone 11D4.1), FITC-conjugated anti-Sca-1 (anti-Ly-6A/E), APC or APCeFluor780-conjugated anti-c-kit (clone 2B8, eBioscience), PECy7-conjugated anti-Thy1.2 (clone 53-2.1), Alexafluor780-conjugated anti-CD11b/Mac1, APC-Cy7 or APC anti-CD19 (clone ID3), PerCP-conjugated GR-1 (anti-Ly6-G, clone RB6-8C5), PerCP or FITC-conjugated anti-B220/CD45R (clone RA3-6B2), PE-conjugated anti-CD25 (clone PC61), FITC-conjugated AA4.1 (clone AA4.1), PE-conjugated anti-VE-Cadherin (clone 16B1, eBioscience), PE-conjugated anti-CD34 (clone RAM34), APC-conjugated anti-CD135 (clone A2F10.1), PE or PE-Cy5-conjugated TER-119 (Ly76, clone TER-119, eBioscience), FITC-conjugated anti-NK1.1 (clone PK136, eBioscience) or corresponding isotype control antibodies. For analysis involving VE-Cadherin antibody (clone 11D4.1), following incubation with primary antibodies, cells were washed twice with PBS/2% FBS and secondary staining was performed with PE-conjugated mouse anti Rat IgG2a (clone RG7/1.30). DAPI was used to exclude dead cells. Flow cytometry was performed on a Becton Dickinson Canto 2 and data analyzed using FlowJo 7.6 Software.

Colony-Forming Unit (CFU) Analysis:

Freshly sorted AGM/PsP or yolk sac cells or cultured cells gently pipetted from wells were washed and counted, re-suspended in IMDM, then added to M3434 methylcellulose semi-solid media containing hematopoietic cytokines (Stem Cell Technologies). Each sample was plated in triplicates. After 7 days of culture, individual colonies were counted and scored by morphology as myeloid (CFU-GM, granulocyte/monocyte; or CFU-Mac, macrophage), erythroid (CFU-E, erythroid; or burst-forming unit, BFU-E, erythroid), or mixed lineage (CFU-GEMM, granulocyte/erythrocyte/monocyte/megakaryocyte). For most analysis, numbers of each CFU type are enumerated per one AGM equivalent of starting cells prior to culture.

Transplantation Assays:

Freshly sorted Ly5.2 AGM cells or cultured cells harvested by gentle pipetting off of wells were washed with PBS with 2% FBS and re-suspended in 100 µl PBS/2% FBS at approximately one AGM equivalent of starting cells per transplanted mouse. Freshly harvested Ly5.1 bone marrow cells were added at 3×104 cells in 100 µl PBS/FBS per mouse to provide short term rescue. Cells were co-injected into lethally irradiated (900-1,000 cGy using a Cesium source) Ly5.1 adult recipients via the tail vein. FACS analysis of peripheral blood obtained by retroorbital bleeds was performed at approximately 3 week intervals. Cells staining for donor Ly5.2 cells with APC-eFluor780 conjugated CD45.2 (clone 104, eBioscience) was distinguished from host/rescue Ly5.1 cells stained with PE-Cy7 conjugated CD45.1 (clone A20, eBioscience) and myeloid and T/B lymphoid lineage determinate was obtained by co-staining with the monoclonal antibodies: FITC-conjugated anti-CD3 (clone 17A2), PE-conjugated F4/80 (clone BM8, eBioscience), APC-conjugated anti-CD19 (clone ID3), and PerCP-conjugated GR-1 (anti-Ly6-G, clone RB6-8C5).

Statistical Analysis:

For statistical analysis, two-tailed paired Student's t-test or two-tailed Student's t-test was used to analyze for significance where indicated, with P value less than 0.05 considered significant.

REFERENCES FOR METHODS

Varnum-Finney B, Halasz L M, Sun M, Gridley T, Radtke F, Bernstein I D. Notch2 governs the rate of generation of mouse long- and short-term repopulating stem cells. J Clin Invest. 2011; 121:1207-1216.

Varnum-Finney B, Wu L, Yu M, et al. Immobilization of Notch ligand, Delta-1, is required for induction of notch signaling. J Cell Sci. 2000; 113 Pt 23:4313-4318.

Varnum-Finney B, Brashem-Stein C, Bernstein I D. Combined effects of Notch signaling and cytokines induce a multiple log increase in precursors with lymphoid and myeloid reconstituting ability. Blood. 2003; 101:1784-1789.

RESULTS, DISCUSSION AND CONCLUSIONS

An important goal in the application of pluripotent stem cells (PSC) for therapeutic purposes is the derivation of hematopoietic stem and progenitor cells (HSPC) capable of efficient engraftment in vivo. Fundamental to achieving this goal is greater understanding of the key signal pathways required to establish, maintain and expand HSPCs from embryonic sources. Ex vivo activation of Notch signaling in mouse bone marrow and human cord blood-derived HSC can facilitate expansion of rapidly engrafting multilineage progenitors, which has recently been translated for therapeutic purposes. In contrast, similar expansion of engrafting cells has not been successful with embryonic stem cell (ESC)-derived hematopoietic precursors.

The study presented in this example evaluated whether embryonic-derived HSPC have capacity to respond to ligand-induced Notch signaling ex vivo, and whether Notch activation could promote expansion of engrafting cells from these embryonic sources. In particular, the study presented herein examined the effects of ex vivo activation of Notch by immobilized, exogenous Notch ligands on highly enriched populations of embryonic HSC and HSC precursors (pre-HSC) at various developmental stages. FIG. 1 shows the general design of the study.

Figure 2A:
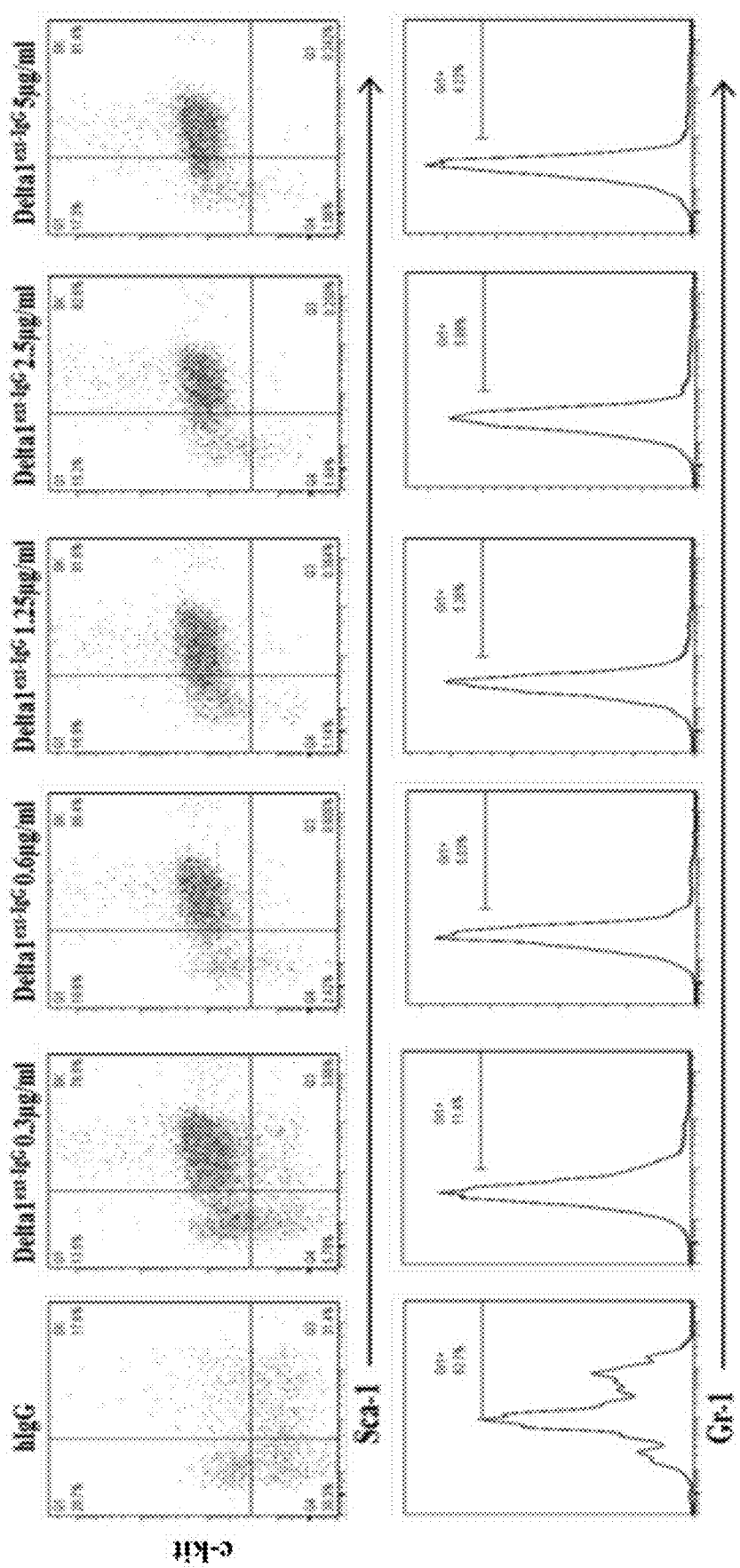
FIGS. 2A-2D show expansion of embryonic hematopoietic stem cells on Notch ligand, Delta1$^{Ext-IgG}$. The mouse AGM (aorta-gonad-mesonephros) was used as a source of embryonic progenitors, by dissection and FACS isolation of VE-Cadherin+/CD45+ cells. Subsequent culture on Delta1$^{ext-IgG}$ with cytokines stem cell factor (SCF), Interleukin-6, 3, and 11 (IL6, IL3, IL11), FLT3-ligand (FLT3L), thrombopoietin (TPO), and 10 µM SB 431542 (TGFβ inhibitor) resulted in expansion of hematopoietic stem/ progenitor by surface phenotype (FIG. 2A), and colonyforming progenitor potential in vitro (FIG. 2B), across a large concentration range of Delta1$^{ext-IgG}$.
Figure 2B:
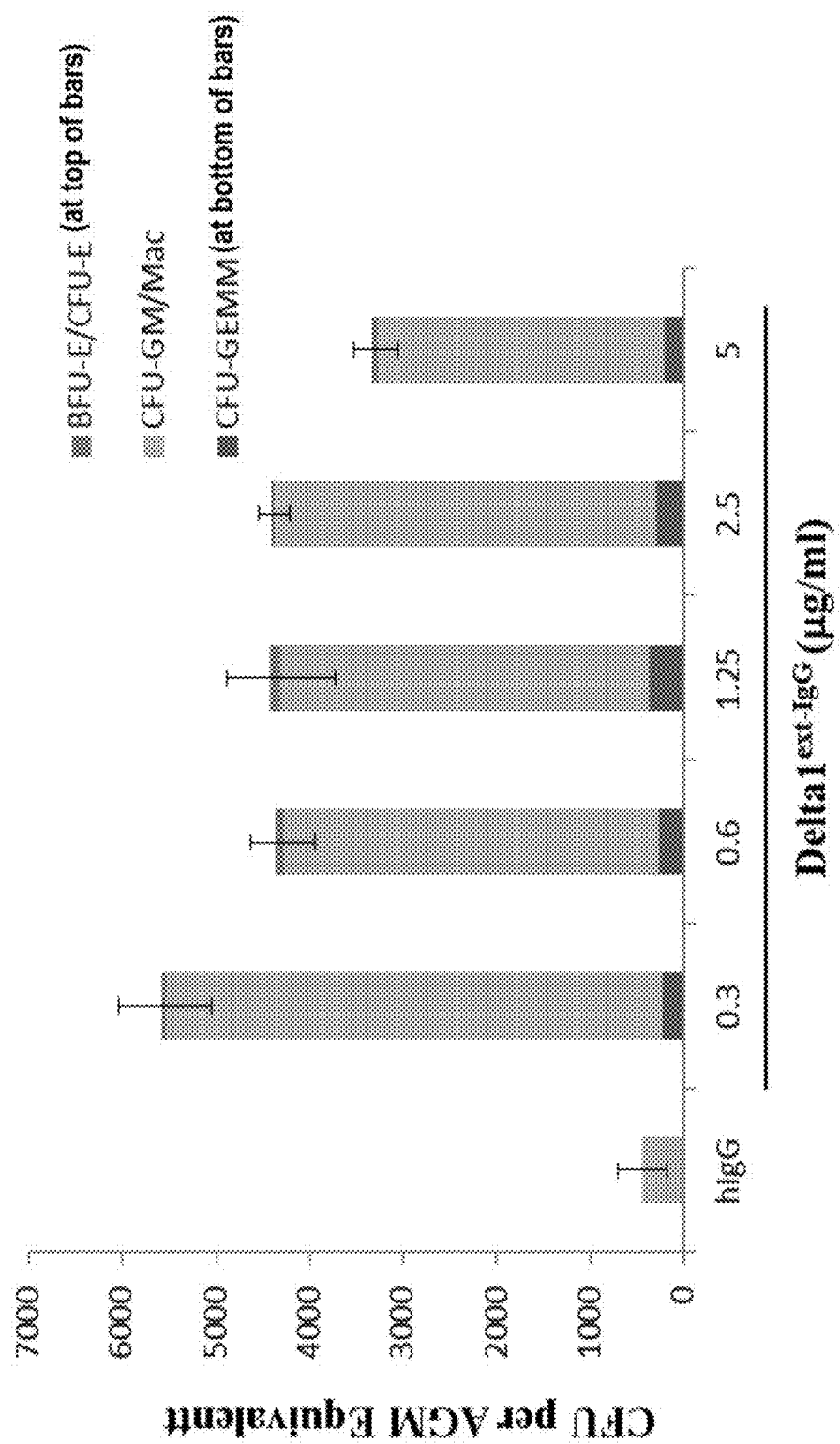
Figure 2C:
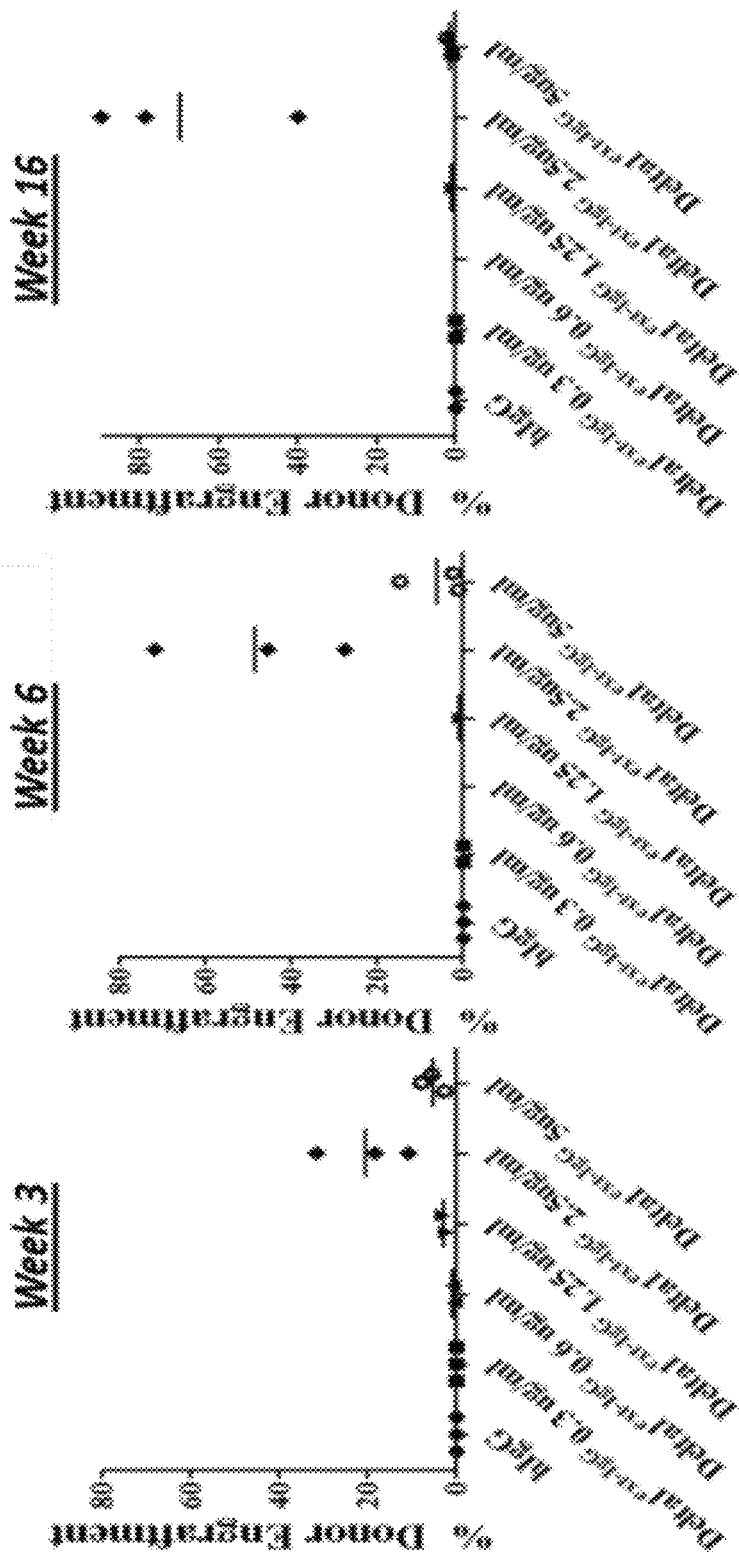
Figure 2D:
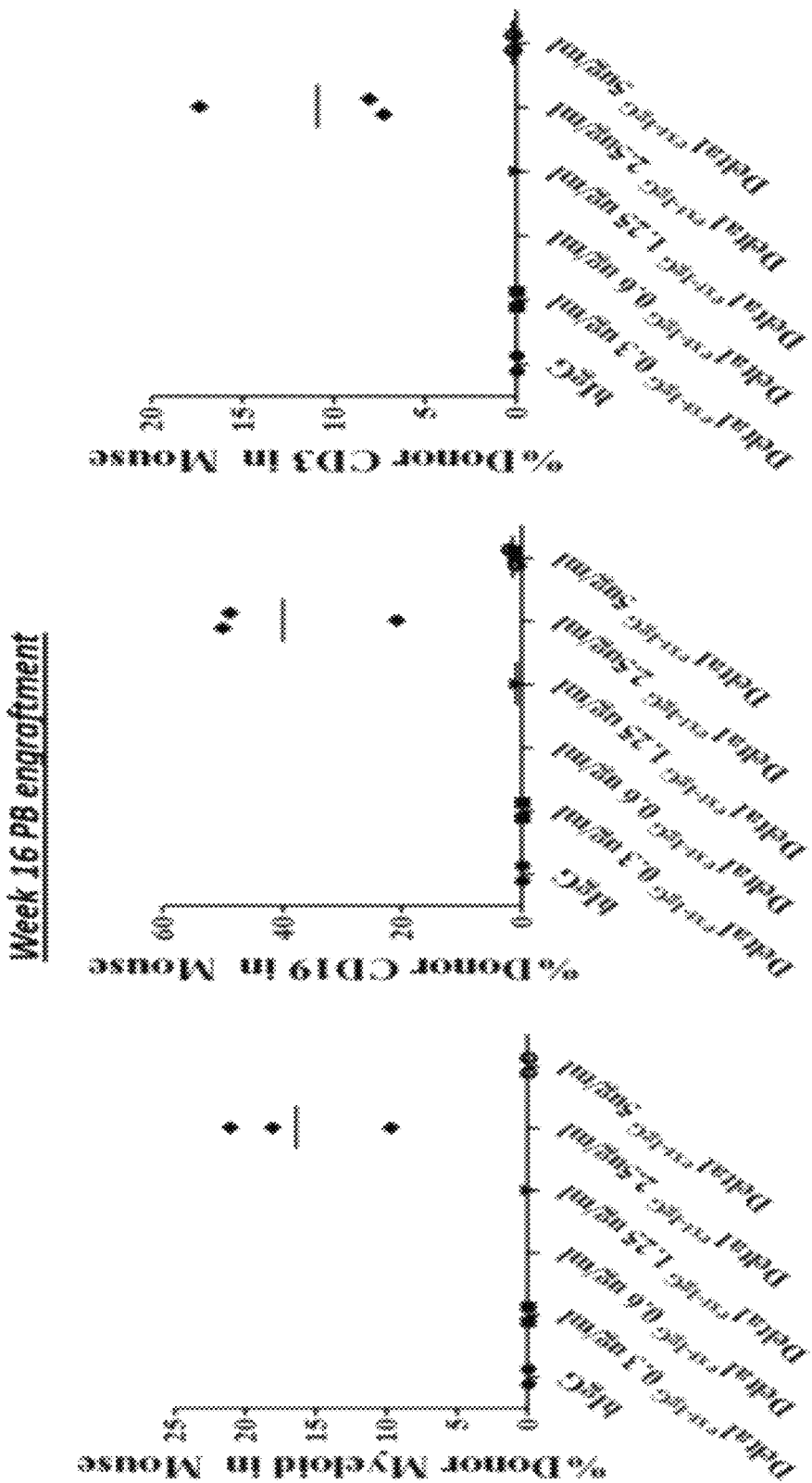

Using a combination of immobilized Notch ligand, Delta1ext-IgG, and hematopoietic cytokines with a small molecule inhibitor of the TGFβ pathway, we have developed a method that enables expansion of hematopoietic stem and progenitor cells from embryonic sources. The mouse AGM (aorta-gonad-mesonephros) was used as a source of embryonic progenitors, by dissection and FACS isolation of VE-Cadherin+/CD45+ cells (see FIG. 1). Subsequent culture of cells on Delta1ext-IgG with cytokines (stem cell factor (SCF), Interleukin-6, 3, and 11 (IL6, IL3, IL11), FLT3-ligand (FLT3L), thrombopoietin (TPO)) and 10 µM SB431542 (TGFβ inhibitor) resulted in expansion of hematopoietic stem/progenitors by surface phenotype (FIG. 2A), and colony-forming progenitor potential in vitro (FIG. 2B), across a large concentration range of Delta1ext-IgG. Key findings of the data are that (i) such expanded cells are capable of long-term, multilineage hematopoietic reconstitution when transplanted into irradiated adult mice, and (ii) such long-term, multilineage hematopoietic reconstitution capacity of expanded progenitors transplanted into irradiated adult mice appears to be sensitive to the dose of Delta1ext-IgG (FIGS. 2C and 2D).

Figure 3A:
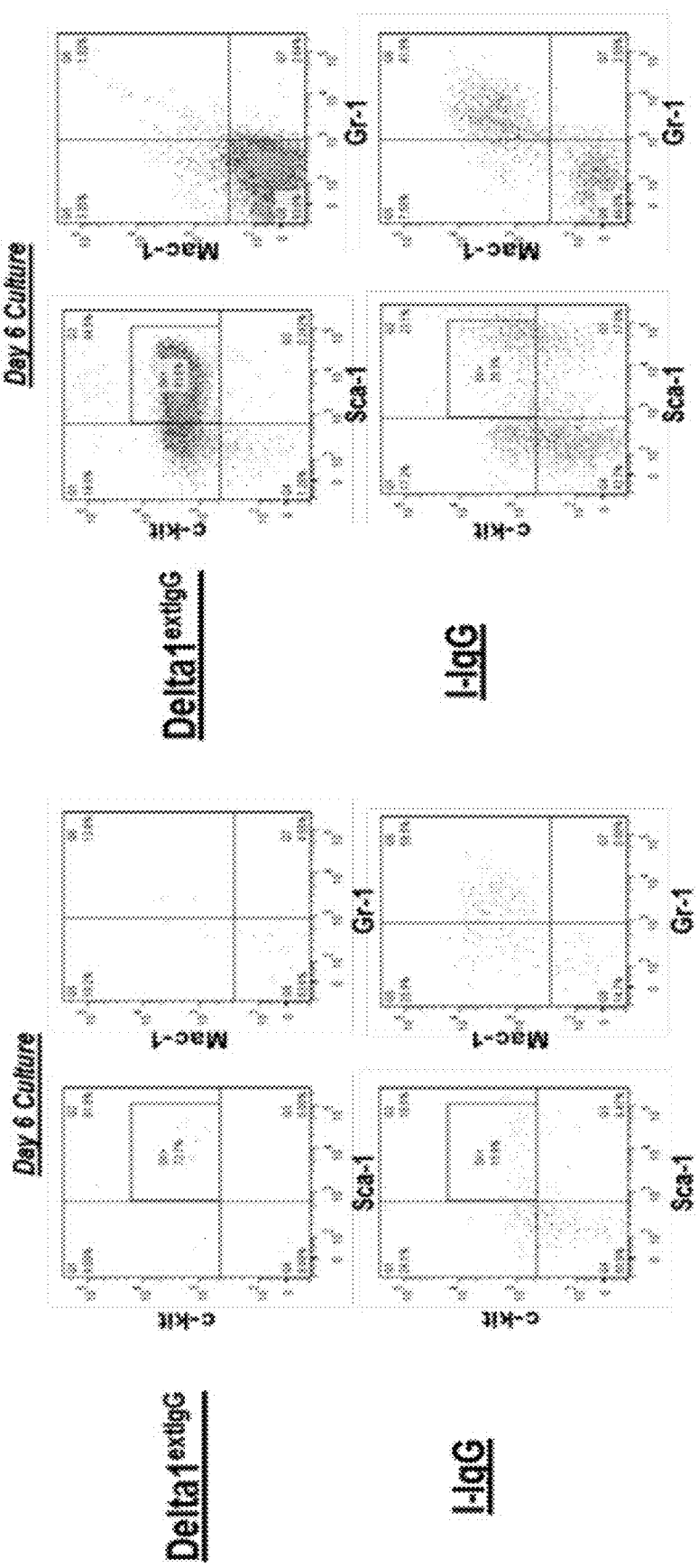
FIGS. 3A-3C show (FIG. 3A) phenotyping and (FIG. 3B) total cells or Sca-1+/c-kit+/Gr1−/Mac1$^{low}$ cells generated from embryonic AGM-derived HSPC (hematopoietic stem/ progenitor cells) expanded on Notch ligand Delta1$^{extIgG}$ (5 µg/ml) or control IgG with media containing cytokines (SCF, TPO, FLT3L, IL3, IL6, IL11) with or without TGF-β inhibitor (SB432542) at 10 µM. SK+=Sca1+/c-kit+.
Figure 3B:
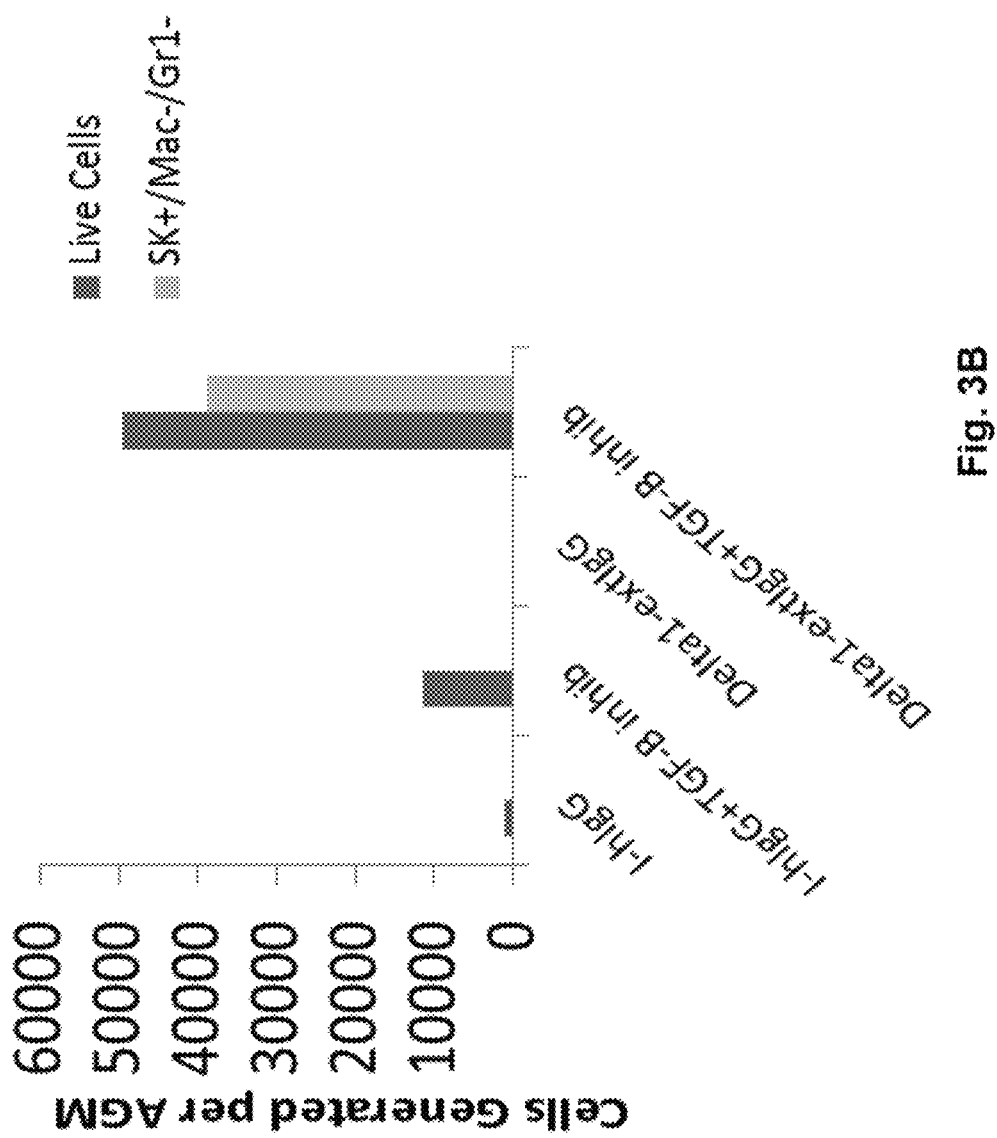
Figure 3C:
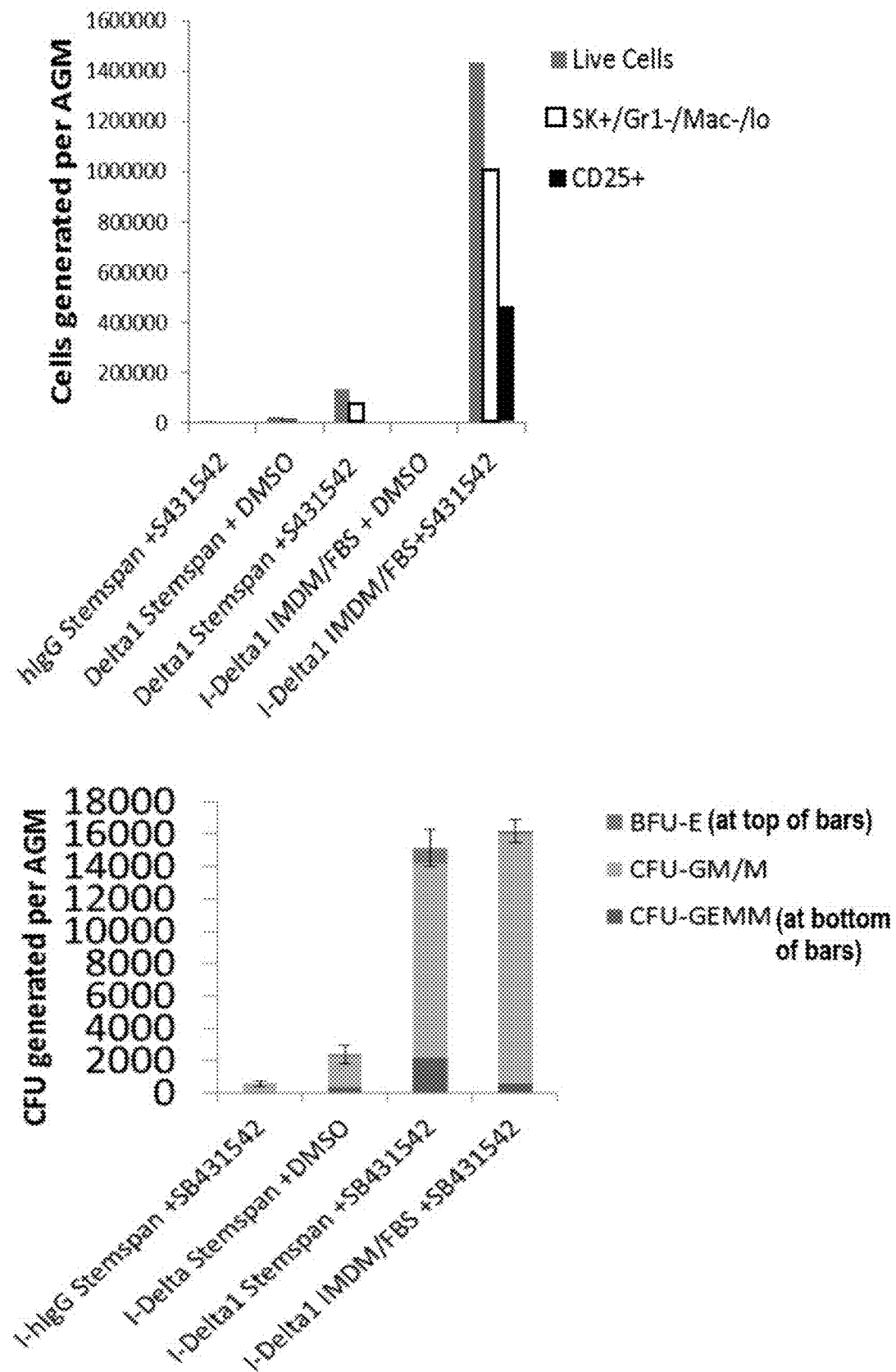

FIGS. 3A-3B presents results of sample experiments showing phenotyping and total cells or Sca-1+/c-kit+/Gr1-/Mac1low progenitor cells generated from embryonic AGM-derived HSPC expanded on Notch ligand Delta1extIgG (which was used at 5 µg/ml in this experiment) or control IgG with media (IMDM/FBS) containing cytokines (SCF, TPO, FLT3L, IL3, IL6, IL11), with or without TGF-β inhibitor (SB432542) at 10 µM (FIGS. 3A and 3B). FIG. 3C presents the results of another representative experiment showing cells and colony-forming progenitors (CFU) generated in experiments with Delta1extIgG (at 5 µg/ml) or control IgG, and SB431542 or control (DMSO), in IMDM/FBS or serum-free media (Stemspan).

Figure 4A:
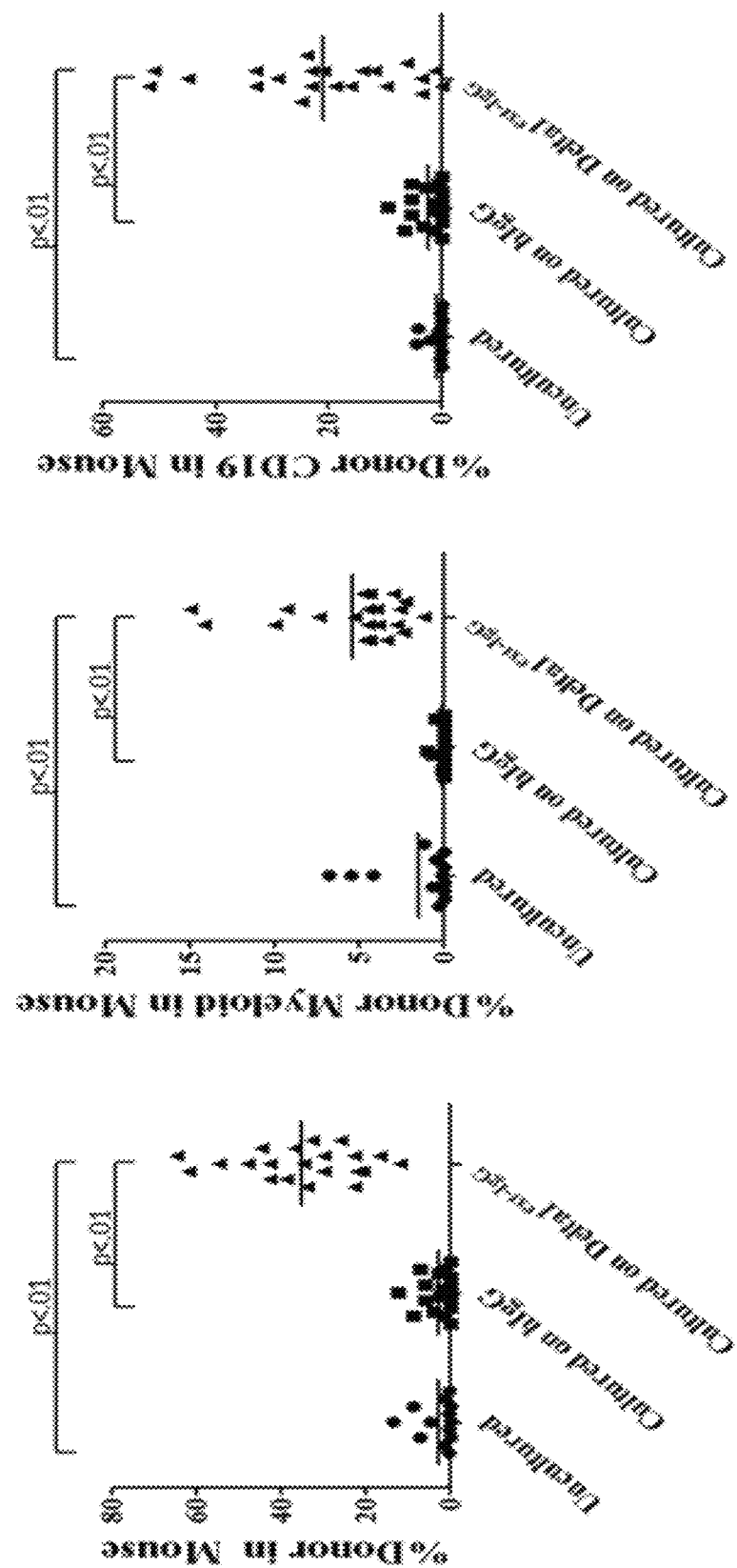
FIGS. 4A-4B show (FIG. 4A) AGM-derived HSPC expanded on Notch ligand Delta1$^{Ext-IgG}$ (using optimized ligand dose 2.5 µg/ml with 6 cytokines and SB431542 as described in FIGS. 2A-2D) demonstrate enhanced, rapidly repopulating myeloid and B lymphoid capacity compared to uncultured cells or cells cultured on control hIgG, when examined at 2 weeks in peripheral blood of competitively transplanted mice. Data is compiled from 5 independent experiments, including 4 experiments with uncultured cells.
Figure 4B:
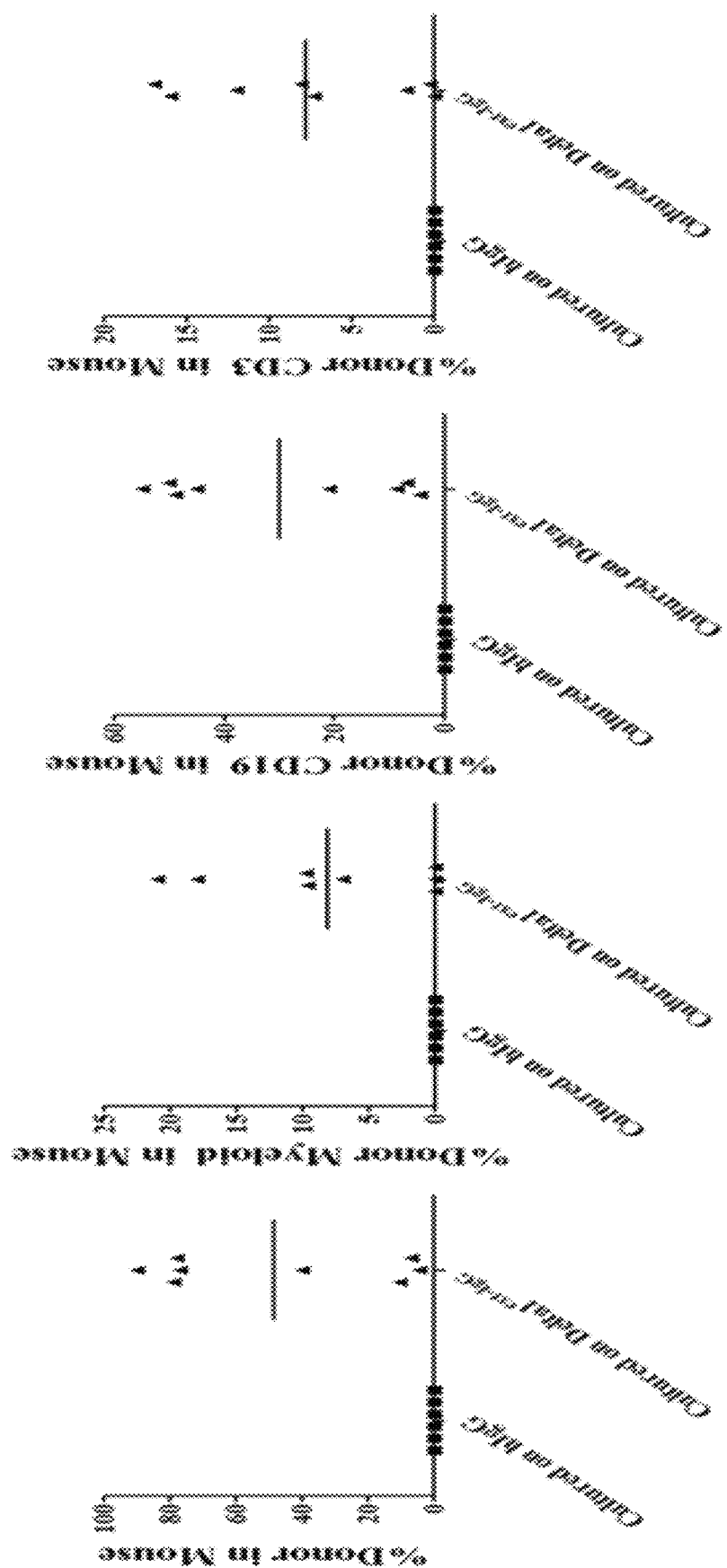

FIG. 4A presents data showing that AGM-derived HSPC expanded on Notch ligand Delta1Ext-IgG (using optimized dose of Delta1Ext-IgG (2.5 µg/ml) with 6 cytokines, SB431542, in IMDM/FBS media as described in relation to FIGS. 1 and 2A-2D) demonstrate enhanced, rapidly repopulating myeloid and B lymphoid capacity compared to uncultured cells or cells cultured on control hIgG, when examined at 2 weeks in peripheral blood of competitively transplanted mice. Data shown in FIG. 4A are compiled from 5 independent experiments, including 4 experiments with uncultured cells. FIG. 4B shows that AGM-derived HSPC expanded on Notch ligand Delta1Ext-IgG (2.5 5 µg/ml) (with 6 cytokines, SB431542, in IMDM/FBS media as described in relation to FIGS. 1 and 2A-2D) maintain long-term multilineage repopulating myeloid and B/T lymphoid capacity compared to cells cultured on control hIgG, when examined at 14-16 weeks in peripheral blood of competitively transplanted mice. Data shown in FIG. 4B are compiled from 3 independent experiments.

Previous studies have successfully manipulated the Notch signaling pathway to expand cord blood derived hematopoietic stem/progenitor cells. The data presented herein unexpectedly demonstrate that this methodology is able to expand the first HSC(s) that develop in the embryo, which form in the AGM region. In particular, the data show that activation of Notch by the ligand Delta1 within HSC/pre-HSC isolated from embryonic aorta-gonad-mesonephros (AGM) promotes expansion of cells with erythromyeloid colony forming potential and T/B-lymphoid potential in vitro, with concurrent maturation of surface phenotype to that resembling fetal liver-stage HSC. Furthermore, the data suggest that Notch activation in embryonic HSPC also mediates expansion of cells with rapidly engrafting myeloid and lymphoid capacity in irradiated mouse models, and that precise activation of Notch signaling by immobilized Notch ligand and cytokines can also support long-term multilineage engraftment from embryonic HSPC expanded in vitro. The results presented in FIGS. 2A-2D, 3A-3C, 4A, and 4B demonstrate that embryonic stage HSPC have capacity to expand in response to Notch activation.

The data suggest that this methodology will have application for expansion of long-term engrafting eHSC from sources such as human embryonic stem cells (ESC), induced pluripotent stem cells (iPSC) or reprogrammed HSC for therapeutic hematopoietic stem cell transplantation into patients and gene therapy of hematopoietic disorders.

This methodology to expand eHSC from ESC, iPSC-derived or reprogrammed HSC would have great impact for expanding such cells for therapeutic and scientific purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references such as patents, patent applications, and publications are cited herein, the disclosures of which are hereby incorporated by reference herein in their entireties.

The invention claimed is:

1. A method of expanding embryonic hematopoietic stem cells, comprising:
   culturing the embryonic hematopoietic stem cells ex vivo in the presence of
   (i) a composition comprising an immobilized Delta or Jagged Notch agonist; and
   (ii) a fluid medium comprising an antibody that inhibits TGFβ and growth factors comprising stem cell factor (SCF), Flt-3 ligand (Flt-3L), Interleukin-3 (IL-3), thrombopoietin (TPO), Interleukin-11 (IL-11), and Interleukin-6 (IL-6);
   thereby producing an expanded embryonic hematopoietic stem cell sample.

2. The method of claim 1, wherein the culturing is not in the presence of an aryl hydrocarbon receptor antagonist.

3. The method of claim 1, wherein the immobilized Delta Notch agonist is an extracellular domain of a Delta protein.

4. The method of claim 3, wherein the extracellular domain is fused to an Fc region of an IgG.

5. The method of claim 3, wherein the Delta protein is a human Delta protein.

6. The method of claim 1, wherein the immobilized Notch agonist is Delta1$^{ext-IgG}$ and wherein Delta1$^{ext-IgG}$ has been applied to a solid phase at a concentration of about 2.5 µg/ml.

7. The method of claim 1, wherein the immobilized Jagged Notch agonist is an extracellular domain of a Jagged protein.

8. The method of claim 1, wherein the SCF and Flt-3L are each in the fluid medium at a concentration between about 10 and 200 ng/ml, and wherein the IL-6 is in the fluid medium at a concentration between about 10 and 100 ng/ml.

9. The method of claim 1, wherein the composition further comprises fibronectin or a fragment thereof.

10. The method of claim 1, wherein the composition further comprises CH-296, and wherein in said culturing step, CH-296 is immobilized on a solid phase.

11. The method of claim 1, wherein the fluid medium further comprises fetal bovine serum (FBS).

12. The method of claim 1, wherein the embryonic hematopoietic stem cells are derived from an embryo, from embryonic stem cells (ESC), from induced pluripotent stem cells (iPSC), or from reprogrammed non-pluripotent cells.

13. The method of claim 1, wherein the embryonic hematopoietic stem cells are derived from induced pluripotent stem cells (iPSC).

14. The method of claim 1, wherein the embryonic hematopoietic stem cells are derived from a single human or more than one human.

15. The method of claim 1, wherein the embryonic hematopoietic stem cells cultured in said culturing step are derived from cells of a patient with a genetic disorder associated with a gene having a sequence defect.

16. The method of claim 1, wherein the embryonic hematopoietic stem cells are derived from the aorta-gonad-mesonephros (AGM) region of an embryo.

17. The method of claim 1, wherein the cells cultured in said culturing step are a population of cells enriched for CD45 and/or VE-Cadherin, in which said embryonic hematopoietic stem cells are present.

18. A method of expanding human embryonic hematopoietic stem cells, comprising culturing the human embryonic hematopoietic stem cells ex vivo on a solid phase coated with Delta1$^{ext-IgG}$ and CH-296, and in the presence of a fluid medium comprising:
   (i) an antibody that inhibits TGFβ; and
   (ii) growth factors comprising SCF, Flt-3L, IL-3, TPO, IL-11, and IL-6; thereby producing an expanded embryonic hematopoietic stem cell sample.

19. The method of claim 18, wherein the Delta1$^{ext-IgG}$ comprises a human Delta1 fragment and a human IgG fragment, the CH-296 is a human fibronectin fragment, and the SCF, Flt-3L and IL-6 are all human.

* * * * *